US012369991B2

(12) United States Patent
Tripathi

(10) Patent No.: US 12,369,991 B2
(45) Date of Patent: *Jul. 29, 2025

(54) REAL-TIME SURGICAL REFERENCE INDICIUM APPARATUS AND METHODS FOR ASTIGMATISM CORRECTION

(71) Applicant: Alcon Inc., Fribourg (CH)

(72) Inventor: Ashok Burton Tripathi, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 287 days.

This patent is subject to a terminal disclaimer.

(21) Appl. No.: 17/938,894

(22) Filed: Oct. 7, 2022

(65) Prior Publication Data

US 2023/0036067 A1 Feb. 2, 2023

Related U.S. Application Data

(60) Continuation of application No. 16/445,936, filed on Jun. 19, 2019, now Pat. No. 11,497,561, which is a
(Continued)

(51) Int. Cl.
*A61B 34/20* (2016.01)
*A61B 3/13* (2006.01)
(Continued)

(52) U.S. Cl.
CPC .............. *A61B 34/20* (2016.02); *A61B 3/13* (2013.01); *A61B 34/10* (2016.02); *A61B 34/25* (2016.02);
(Continued)

(58) Field of Classification Search
CPC ......... A61B 34/20; A61B 34/10; A61B 34/25; A61B 90/20; A61B 90/37;
(Continued)

(56) References Cited

U.S. PATENT DOCUMENTS 5,715,836 A * 2/1998 Kliegis ................ G16H 20/40
600/425
9,414,961 B2 * 8/2016 Tripathi ................ A61B 34/25
(Continued)

*Primary Examiner* — Vi X Nguyen
(74) *Attorney, Agent, or Firm* — Quinn IP Law

(57) ABSTRACT

A system, method, and apparatus for guiding an astigmatism correction procedure on an eye of a patient are disclosed. An example apparatus includes a photosensor configured to record a pre-operative still image of an ocular target surgical site of the patient. The apparatus also includes a real-time, multidimensional visualization module configured to produce a real-time multidimensional visualization of the ocular target surgical site during an astigmatism correction procedure. The apparatus further includes a data processor configured to determine a virtual indicium that includes data for guiding the astigmatism correction procedure. The data processor uses the pre-operative still image to align the virtual indicium with the multidimensional visualization such that the virtual indicium is rotationally accurate. The data processor then displays the multidimensional visualization of the ocular target surgical site in conjunction with the virtual indicium.

7 Claims, 12 Drawing Sheets

Related U.S. Application Data division of application No. 15/234,276, filed on Aug. 11, 2016, now Pat. No. 10,368,948, which is a continuation of application No. 14/327,329, filed on Jul. 9, 2014, now Pat. No. 9,414,961, which is a division of application No. 12/582,671, filed on Oct. 20, 2009, now Pat. No. 8,784,443.

(51) Int. Cl.
*A61B 34/00* (2016.01)
*A61B 34/10* (2016.01)
*A61B 90/00* (2016.01)
*A61B 90/20* (2016.01)
*A61F 9/007* (2006.01)
*A61F 9/013* (2006.01)

(52) U.S. Cl.
CPC ............ *A61B 90/20* (2016.02); *A61B 90/37* (2016.02); *A61F 9/007* (2013.01); *A61F 9/0136* (2013.01); *A61B 2034/107* (2016.02); *A61B 2034/2057* (2016.02); *A61B 2034/2065* (2016.02); *A61B 2090/0807* (2016.02); *A61B 2090/3612* (2016.02); *A61B 2090/365* (2016.02); *A61B 2090/373* (2016.02); *A61B 2576/00* (2013.01)

(58) Field of Classification Search
CPC ....... A61B 2034/107; A61B 2034/2065; A61F 9/013; A61F 9/007; A61F 9/0136
See application file for complete search history.

(56) References Cited

U.S. PATENT DOCUMENTS

| | | | |
|---|---|---|---|
| 11,497,561 B2 * | 11/2022 | Tripathi | .................. A61B 90/20 |
| 2008/0103367 A1 * | 5/2008 | Burba | ..................... A61F 9/007 |
| | | | 600/236 |

* cited by examiner

REAL-TIME SURGICAL REFERENCE INDICIUM APPARATUS AND METHODS FOR ASTIGMATISM CORRECTION

PRIORITY CLAIM

The present application claims priority to and benefit of U.S. patent application Ser. No. 16/445,936 (US Pub 20190298459A1), filed Jun. 19, 2019, which is a divisional of U.S. patent application Ser. No. 15/234,276, filed on Aug. 11, 2016, now U.S. Pat. No. 10,368,948. The U.S. patent application Ser. No. 15/234,276 is a continuation of, claims priority to, and the benefit of U.S. patent application Ser. No. 14/327,329, filed on Jul. 9, 2014, now U.S. Pat. No. 9,414,961, which is a divisional of, claims priority to, and the benefit of U.S. patent application Ser. No. 12/582,671, filed on Oct. 20, 2009, now U.S. Pat. No. 8,784,443. The entirety of each application listed above is incorporated herein by reference.

FIELD OF THE INVENTION

The present description generally relates to the field of ocular surgery, and more particularly to ocular surgical procedures utilizing visual imaging systems including open or unmagnified surgery and micro-surgery, such as correction of astigmatism, utilizing visual imaging systems with magnification.

BACKGROUND

Ocular surgery, particularly when involving vision correction, is highly patient specific, being dependent on specific features and dimensions that in certain cases may be significantly different from those of expected norms. As a result, surgeons must rely upon their individual experience and skills to adapt whatever surgical techniques they are practicing to the individual requirements as determined by each patient's unique ocular structural features and dimensions.

To date, this individualized surgical adaptation is often accomplished essentially through freehand and best guess techniques based upon a pre-surgery examination and evaluation of each individual's ocular region and specific ocular features. This pre-surgical examination may include preliminary measurements as well as the surgeon making reference markings directly on the patient's ocular tissues with a pen or other form of dye or ink marking. Then, after the patient has been prepared and placed in a supine or prone position for surgery, as opposed to the often vertical seated positioning of the patient during the pre-surgery examinations, the surgeon adapts the placement and configuration of the initial surgical incisions to the actual physical dimensions and circumstances found in the patient as the surgical procedure begins and progresses.

Further complicating matters, ocular tissues are not conducive to pre-surgery reference markings or measurements. This is particularly true because most ocular tissues have wet surfaces diminishing the quality of reference markings. Even further still, many ocular surgeries involve internal physical structures that cannot be accessed for direct measurement or marking prior to surgery, and therefore, the pre-surgical markings on external surfaces must be visually translated onto the internal structures actually being modified. This translation often leads to undesirable post-surgical outcomes.

Additionally, pre-surgical rinsing, sterilization, or drug administration to the ocular tissues prior to or during surgery may dissolve, alter or even remove reference markings. Similarly, subsequent wiping and contact with fluids, including the patient's body fluids, during the surgical procedure may remove or distort any reference markings from the ocular region of interest. As a result, surgical reference markings may lose any practical effectiveness beyond the initial stages of the surgical procedure and in and of themselves are not accurate as they present broad lines to indicate, in some procedures, micro-sized incisions.

As such, there is a continuing need for effective reference indicia properly aligned with one or more particular ocular axis, especially when proper alignment of pre-surgical data is pivotal to satisfactory patient outcome. For instance, accurate rotational alignment of pre-surgical data with the ocular surgery is highly advantageous when making one or more limbal relaxing incisions on an eye to correct for varying degrees of astigmatism.

Astigmatism correction is a highly sophisticated surgical procedure that relies on delicate incisions within or on the limbus or cornea of an eye commonly known as limbal relaxing incisions (LRI) or astigmatic keratotomy (AK) to correct for a non-spherical topography of the eye. In the past, this delicate procedure has been performed based on partially accurate or even inaccurate visual measurements coupled with calculated incision templates based on those inaccurate visual measurements of a patient's eye. Past procedures have commonly relied on visual measurements prior to surgery and the subsequent inaccurate translation of those measurements to the limbal relaxing incision procedures where the positioning of the measured axis of the eye may have rotated and shifted. As a result, it is not uncommon for the placement of limbal or corneal relaxing incisions to be improperly aligned with the natural vertical axis of the eye, thereby resulting in residual astigmatism requiring glasses, and can include such side effects as poor visual acuity and shadows under low ambient light conditions.

Accordingly, in spite of the ongoing development and the growing sophistication of contemporary ocular surgery, there is a continuing need for the provision of effective reference indicia including data for making at least one limbal or corneal relaxing incision which is rotationally accurate relative to a patient's natural vertical axis or other important axis of orientation.

SUMMARY

The apparatus and methods described herein address the long-felt need for functional, useful, and effective ocular surgery reference markings, or indicia, including data or information for making at least one ocular relaxing incision in an astigmatism correction surgery. The ocular relaxing incisions described herein can be on or within the limbus or cornea of an eye, or both, for example, a limbal relaxing incision (LRI) or a corneal relaxing incision (CRI). Further, provided are apparatus and associated methods for the generation of at least one rotationally accurate and effective, real-time, virtual reference indicium including data for making at least one ocular, e.g. limbal or corneal, relaxing incision in conjunction with at least one real-time, multidimensional visualization of a target surgical field, or at least a portion thereof, throughout a surgical procedure or any subpart thereof. In one embodiment, the multidimensional visualizations can be three dimensional (3D), stereoscopic, and high definition (HD). In other embodiments, portions of the imaging described herein can be performed in two dimensions.

Moreover, the virtual reference indicium, or multiple reference indicia, including data for making at least one limbal and/or corneal relaxing incision can be automated, but are placed under the direct control, adjustment, and verification of the operating surgeon or surgical team. This control enables the operating surgeon or surgical team to fine tune the virtual reference indicia including data for making at least one limbal and/or corneal relaxing incision as desired or needed and to align and lock the reference indicium in place relative to the individual patient's target ocular anatomy. Once so aligned, the virtual reference indicia including data for making at least one limbal and/or corneal relaxing incision function as effective guides or references for the surgeon or surgical team throughout the duration of an entire astigmatism correcting procedure or any subpart thereof.

Even further, the apparatus and methods described herein make it possible for an operating surgeon to directly remove and reinstate at least one real-time, virtual surgical reference indicium or indicia including data for making at least one limbal and/or corneal relaxing incision as needed at any time throughout the duration of astigmatism correcting procedure at the control of and in response to the needs of the operating surgeon. An operating surgeon can also utilize multiple, different real-time, virtual reference indicia or data for making at least one limbal and/or corneal relaxing incision sequentially or simultaneously. Additionally, the apparatus and methods described herein also make it possible for the operating surgeon to replace at least one initial real-time, virtual reference indicium including data for making at least one limbal and/or corneal relaxing incision with one or more secondary or modified real-time, virtual reference indicia at an appropriate time during the surgical procedure to provide additional surgical guidance in real-time as desired or needed throughout the procedure.

Exemplary apparatus and associated methods described herein accomplish these previously unobtainable benefits through the utilization of at least one real-time, multidimensional visualization module such as the TrueVision Systems, Inc. real-time 3D HD visualization systems as disclosed and claimed in the Applicant's co-pending patent applications made of reference herein. These exemplary multidimensional visualization modules function as either retrofit devices attached to existing stereomicroscopes in place of traditional microscope binocular optics or as standalone stereoscopic 3D HD visualization apparatus. These exemplary apparatus can include various optical or electronic magnification systems including stereomicroscopes or can function as open surgery apparatus utilizing overhead cameras with or without magnification.

In conjunction with the multidimensional visualization module, the apparatus includes at least one data processor such as a computer or microprocessor with appropriate software which is configured to produce in real-time, one or more virtual reference indicium including data for making at least one limbal and/or corneal relaxing incision in conjunction with the real-time visualization of the target surgical field produced by the exemplary multidimensional visualization module. The data processor is provided with at least one user control input enabling the operating surgeon, or surgical team, to adjust all, or at least portions of the pre-operative patient data, including, for example, a still image of an eye, to verify and lock its alignment relative to the multidimensional visualization of the surgical field or to suit the needs or desires of the surgeon or surgical team before or during the surgical procedure involved.

Further, the real-time, virtual reference indicium including data for making at least one limbal and/or corneal relaxing incision are generated by the at least one data processor utilizing pre-operative patient data. Exemplary pre-operative patient data used to generate the at least one real-time virtual reference indicium including data for making at least one limbal and/or corneal relaxing incision is generally in the form of a pre-operative still image of an eye or, preferably an HD still image, portion of a video clip, or alternatively, an HD photograph, all of which may be stereoscopic 3D images.

Further still, in one embodiment, the HD still image, photo or pre-operative patient data is reviewed or scanned to identify at least one specifically identifiable or distinguishing visual feature such as a scar, vascular pattern, or physical structure found within the target surgical field that is static with respect to the tissues or structures of interest in the surgical procedure. For example, the boundary of the pupil is an easily identifiable physical feature present in all eyes. Another example of a visual feature might be a dense vascular area in the sclera, or white portion, of the eye. Such an identifiable visual feature or combination of features is used to align and lock the HD still image or pre-operative patient data in place with the real-time multidimensional visualization of the target surgical field before and during the surgical process to avoid misalignment due to natural structural shifts or rotations within the target surgical field.

In further accordance with the teachings of the present description, the pre-operative still image of an eye, now aligned and locked with the real-time multidimensional visualization of the target surgical field is modified to include at least one virtual reference indicium, including data for making at least one limbal relaxing incision and/or at least one corneal relaxing incision, which is uniquely suited for an astigmatism correction procedure and the specific patient's target anatomy. This modification is accomplished by the data processor or, alternatively, by a second dedicated data processor for generating the virtual reference indicium or multiple reference indicia including data for making at least one limbal and/or corneal relaxing incision, or by combinations thereof as determined by the surgeon or surgical team. Once incorporated into position, the at least one real-time, virtual surgical reference indicium functions as a reference or guide to assist the surgeon performing the relevant portion of a surgical procedure in spite of the possibility that the target surgical field may have moved or re-oriented relative to other patient physical features or structures after the still image or pre-operative patient data is captured or obtained. Additionally, the included data for making at least one limbal or corneal relaxing incision can track the natural vertical axis of an eye, relative to the target surgical field. The combination of at least one virtual reference indicium with data for making at least one limbal and/or corneal relaxing incision allows a surgeon to utilize the guidance provided by the virtual reference indicia while being aligned and locked in a position that is rotationally accurate when compared to the natural vertical axis of an eye.

It should be noted that the real-time, virtual surgical reference indicia and data for making at least one limbal and/or corneal relaxing incision can be presented as two dimensional (2D) or 3D indicia as appropriate or desired. For example, a virtual reference indicium intended to direct a surgical incision of a relative flat tissue can be presented as a 2D line incorporated into the multidimensional or 3D visualization provided by the visualization module. Surgeons may prefer 3D indicium or natural patient vertical when operating on more complex shapes and surfaces.

The surgeon is able to utilize the reference indicium including data for making at least one limbal and/or corneal relaxing incision as a pattern or guide which is aligned and rotationally accurate and locked into the eye's natural vertical axis. In order to make the proper limbal or corneal relaxing incisions, the virtual indicium is accurately dimensioned and rotationally aligned with the eye's natural vertical axis and visual features of the eye, and incorporated into the 3D HD visualization, rather than being marked directly onto the exterior of the patient's eye as in the prior art where it would at best be an approximation of the incision locations.

Further advantages and features of the apparatus and methods described herein will be provided to those skilled in the art from a consideration of the following Detailed Description taken in conjunction with the associated Figures, which will first be described briefly.

DETAILED DESCRIPTION

Figure 1:
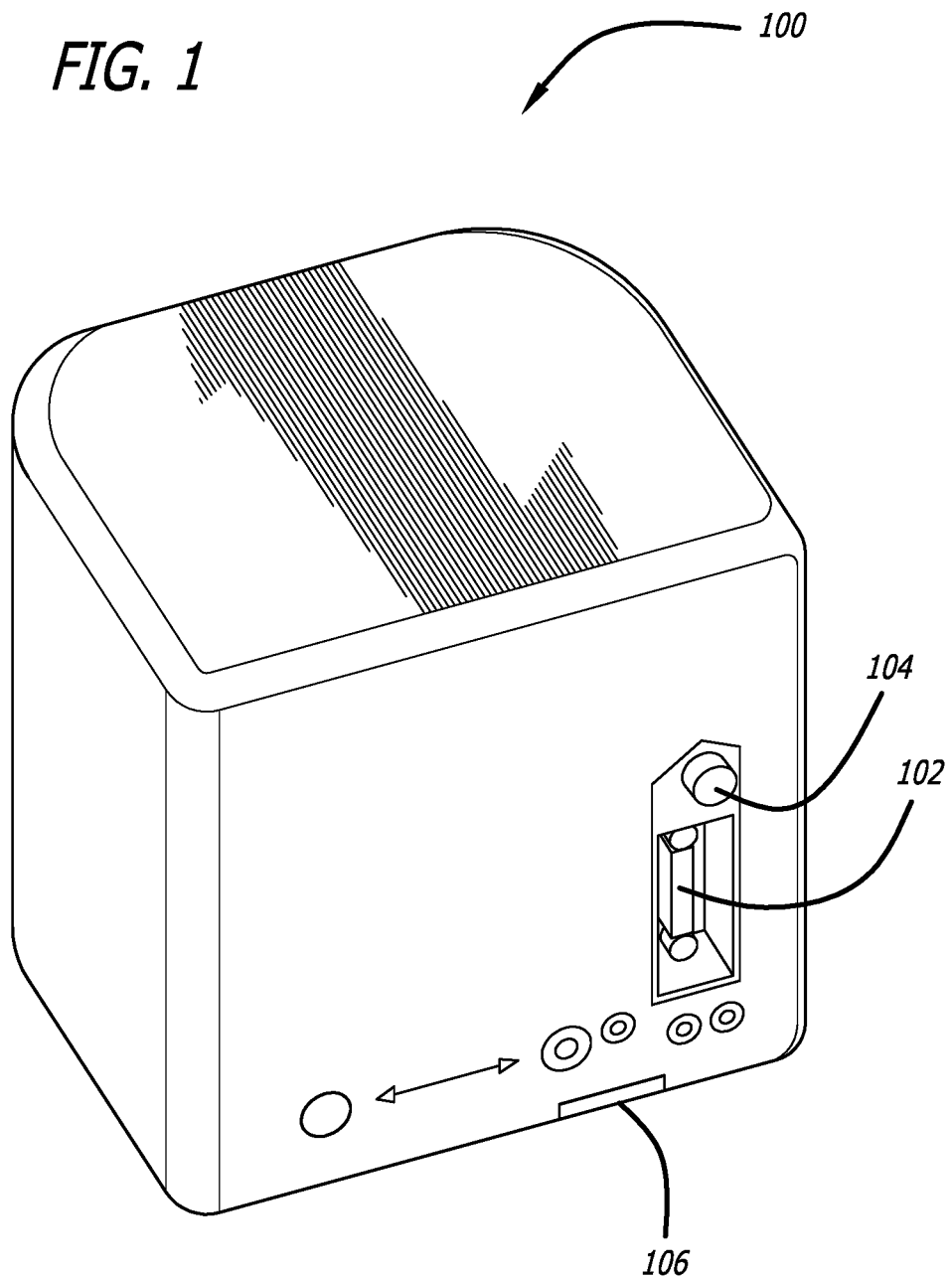
FIG. 1 is an illustration of an exemplary image capture module of the present description.

Described herein are apparatus and methods for generating one or more rotationally accurate, real-time, virtual reference indicium, or multiple indicia, including data for making at least one ocular relaxing incision in conjunction with at least one real-time, multidimensional visualization of at least a portion of a target surgical field throughout a surgical procedure or any subpart thereof. The ocular relaxing incisions described herein can be on or within the limbus or cornea of an eye, or both, for example, a limbal relaxing incision (LRI) or a corneal relaxing incision (CRI), also known as astigmatic keratotomy (AK). In some embodiments, at least one element of the imaging described herein is stereoscopic. In one embodiment, the multidimensional visualization is stereoscopic three-dimensional (3D) video and also may be in high definition (HD). Those skilled in the art will appreciate that a 3D HD real-time visualization will be most effective in enabling a physician to perform an astigmatism correcting procedure. However, two dimensional (2D) systems or portions thereof can be useful according to the present description.

Moreover, the virtual reference indicia including data for making at least one limbal and/or corneal relaxing incision can be placed under the direct control and adjustment of the operating surgeon or surgical team, thereby enabling the surgeon to have tight control over the reference indicia and properly align it to an eye's natural vertical axis. Once the surgeon has aligned the virtual reference indicia including data for making at least one limbal and/or corneal relaxing incision, it can be locked in place and act as an effective guide for the surgeon throughout any or all portions of a surgical procedure at the discretion and control of the surgeon or surgical tem.

"Rotationally accurate" as used herein refers to a systems ability to properly track an eye's natural vertical axis (also referred to as a patient's ocular natural vertical axis). As such, the at least one virtual reference indicia including data for making at least one limbal and/or corneal relaxing incision described herein is rotated accurately relative to the eye's natural vertical axis. Accuracy of the systems and methods described herein for rotationally tracking the natural vertical axis is within less than about 1 degree in other embodiments, the accuracy can be within less than about a half a degree or a quarter of a degree. The virtual reference indicia can also include information about the eye's natural vertical axis in addition to accurately tracking it. Virtual reference indicia including data for making at least one limbal and/or corneal relaxing incision are further described in the embodiments of the present description.

As an added benefit, the real-time virtual reference indicia including data for making at least one limbal and/or corneal relaxing incision can be positioned accurately at the appropriate depth within the target surgical field to precisely indicate the correct reference indicium size, shape, and position on the tissue or tissues of interest as well as accurately align the surgical procedure with the natural vertical axis of the eye. Further, varying real-time virtual reference indicia including data for making at least one limbal and/or corneal relaxing incision can be generated within the real-time multidimensional visualization as appropriate during different phases of the surgical procedure where different ocular tissues or structures are subsequently targeted or exposed, or to track moving ocular tissues or structures in real-time and to realign the real-time virtual reference indicia as appropriate. Additionally, the color, luminosity, transparency, or other visual characteristics of the virtual reference indicia and data for making at least one limbal and/or corneal relaxing incision may be altered by a surgeon or at least one data processor as appropriate to enhance their contrast and visibility relative to the colors and textures of the actual target surgical site to assist the surgeon in performing the surgical procedure.

In a broad aspect, illustrating these beneficial features, an exemplary apparatus incorporates three primary elements: at least one real-time multidimensional visualization module, at least one data processor, and at least one user control input. The three elements can be physically combined into a single device or can be linked as physically separate elements within the scope and teachings of the present disclosure as required by the specific surgical procedure being practiced.

An exemplary real-time multidimensional visualization module suitable for practicing the present methods incorporates the basic structural components of the Applicant's TrueVision Systems, Inc. real-time 3D HD visualization systems described in the Applicant's co-pending U.S. application Ser. No. 11/256,497 entitled "Stereoscopic Image Acquisition Device," filed Oct. 21, 2005; Ser. No. 11/668,400 entitled "Stereoscopic Electronic Microscope Workstation," filed Jan. 29, 2007; Ser. No. 11/668,420 entitled "Stereoscopic Electronic Microscope Workstation," filed Jan. 29, 2007; Ser. No. 11/739,042 entitled "Stereoscopic Display Cart and System," filed Apr. 23, 2007; and Ser. No. 12/417,115, entitled "Apparatus and Methods for Performing Enhanced Visually Directed Procedures Under Low Ambient Light Conditions," filed Apr. 2, 2009, all of which are fully incorporated herein by reference as if part of this specification.

The multidimensional visualization module is used to provide a surgeon with a real-time visualization of at least a portion of a target surgical field, which in the present application is an eye.

"Real-time" as used herein generally refers to the updating of information at essentially the same rate as the data is received. More specifically, "real-time" is intended to mean that the image data is acquired, processed, and transmitted from the photosensor of the visualization module at a high enough data rate and at a low enough time delay that when the data is displayed, objects presented in the visualization move smoothly without user-noticeable judder, latency or lag. Typically, this occurs when the processing of the video signal has no more than about $\frac{1}{10}^{th}$ second of delay.

It should be appreciated that while it is preferred to utilize a multidimensional visualization module that provides a surgeon with a real-time 3D visualization of at least a portion of the target surgical field, it is contemplated as being within the scope of the present disclosure for the visualization module to provide a real-time visualization that is a real-time 2D visualization. However, the use of a 3D visualization is preferred as it provides many benefits to the surgeon including more effective visualization and depth of field particularly with regard to the topography of an eye. In one embodiment, the visualization of the target surgical field is in high definition (HD).

The term "high definition" or "HD" as used herein can encompass a video signal having a resolution of at least 960 lines by 720 lines and to generally have a higher resolution than a standard definition (SD) video. For purposes of the present invention, this can be accomplished with display resolutions of 1280 lines by 720 lines (720p and 720i) or 1920 lines by 1080 lines (1080p or 1080i). In contrast, standard definition (SD) video typically has a resolution of 640 lines by 480 lines (480i or 480p) or less. It is however, within the scope of the present description that the multidimensional visualization can be in SD, though HD is preferred.

The apparatuses described herein can be embodied in a single device which can be retrofitted onto existing surgical equipment such as surgical microscopes or open surgery apparatus. This is highly advantageous as retrofit embodiments can be added to existing systems, allowing expensive equipment to simply be upgraded as opposed to purchasing an entirely new system. The exemplary apparatus can include various optical or electronic magnification systems including stereomicroscopes or can function as open surgery apparatus utilizing cameras and overhead visualizations with or without magnification.

FIG. 1 illustrates image capture module 100 which includes a multidimensional visualization module and an image processing unit, both housed within image capture module 100, and therefore, not depicted. The exemplary image capture module comprises at least one photosensor to capture still images, photographs or videos. As those skilled in the art will appreciate, a photosensor is an electromagnetic device that responds to light and produces or converts light energy into an electrical signal which can be transmitted to a receiver for signal processing or other operations and ultimately read by an instrument or an observer. Communication with image capture module 100 including control thereof and display output from image capture module 100 are provided by first connector 102. Image capture module power is provided by second connector 104. Additionally, image capture module 100 can manually control the transmitted light intensity using iris slider switch 106.

Figure 2:
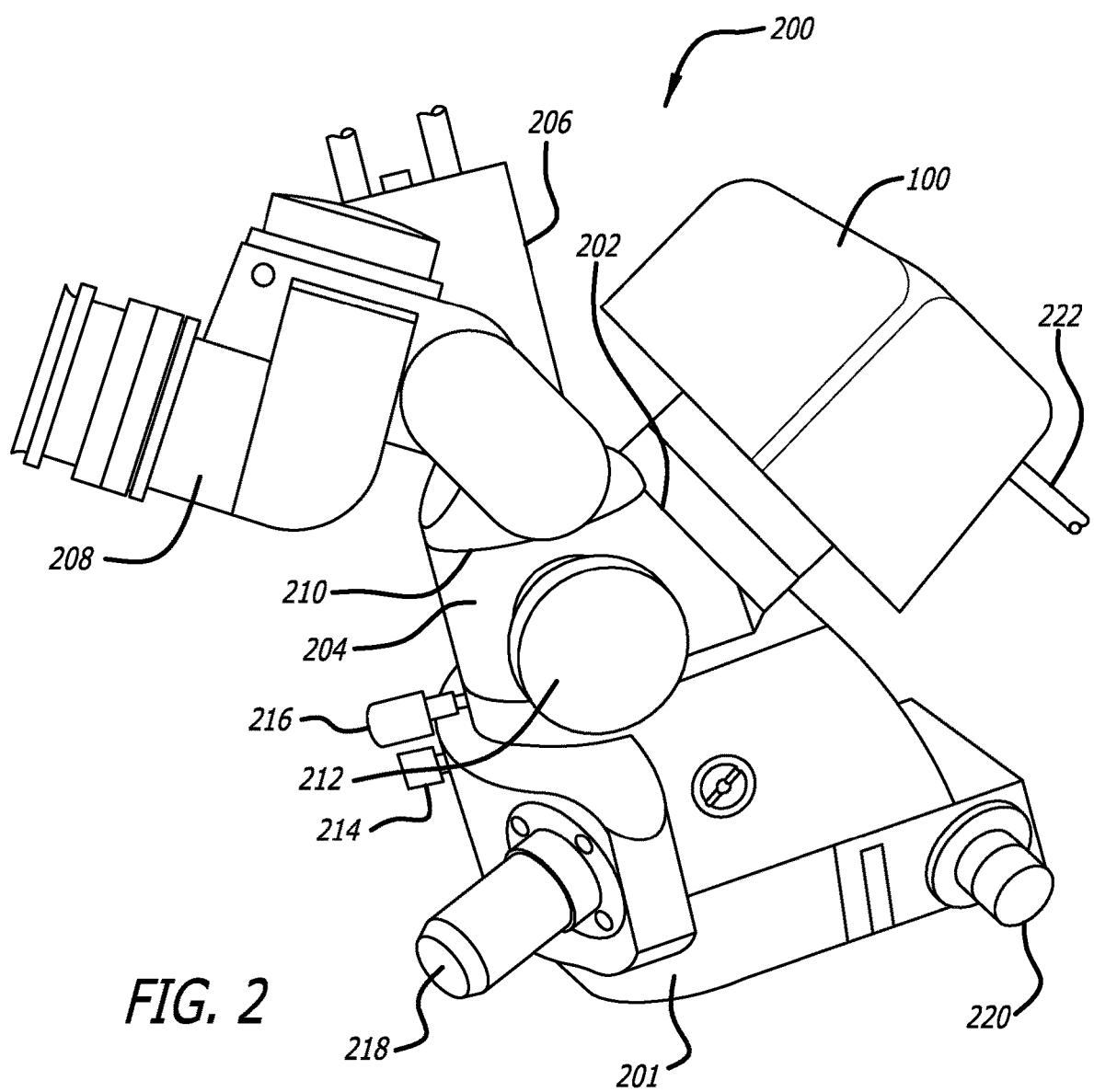
FIG. 2 is an illustration of an exemplary apparatus of the present description retrofitted on a surgical microscope.

In another embodiment, FIG. 2 illustrates retrofitted surgical microscope 200 incorporating image capture module 100 retrofitted thereto. Retrofitted surgical microscope 200 includes image capture module 100 coupled to first ocular port 202 on ocular bridge 204. Further, ocular bridge 204 couples video camera 206 to a second ocular port (not shown) and binocular eyepiece 208 to third ocular port 210. Optional forth ocular port 212 is available for further additions to retrofitted surgical microscope 200. Although retrofitted surgical microscope 200 includes image capture module 100, it still retains the use of conventional controls and features such as, but not limited to, iris adjustment knob 214, first adjustment knob 216, second adjustment knob 218, illumination control knob 220, and an objective lens (not shown) Further still, image capture module 100 can send and receive information through signal cable 222 which is connected to first connector 102, while power is supplied via second connector 104 of image capture module 100.

Figure 3:
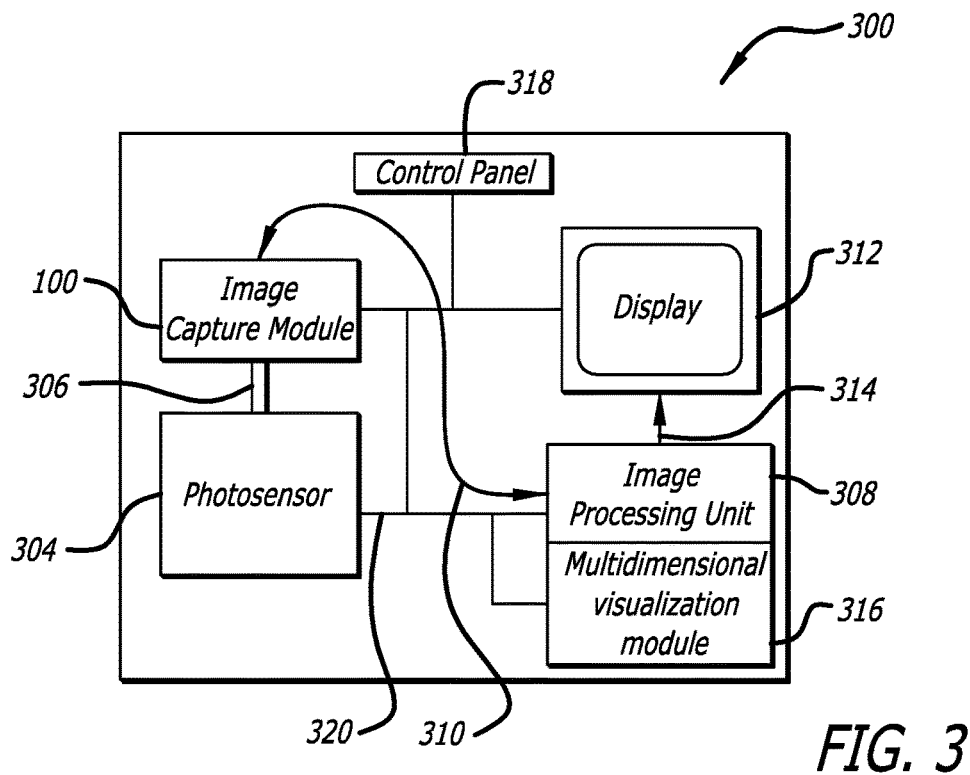
FIG. 3 is a schematic overview of an exemplary embodiment of an apparatus of the present description illustrating features thereof.

An exemplary, non-limiting configuration of components is illustrated in FIG. 3. Apparatus setup 300 includes image capture module 100, coupled to photosensor 304 by bi-directional link 306. Those skilled in the art will appreciate that bi-directional link 306 can be eliminated where image capture module 100 and photosensor 304 are physically the same device. Image capture module 100 is in direct communication with image processing unit 308 by first cable 310. First cable 310 can be a cable connecting to physically different devices, can be a cable connecting two physically different components within the same device, or can be eliminated if image capture module 100 and image processing unit 308 are physically the same device. First cable 310 allows, in certain embodiments, bi-directional communication between image capture module 100 and image processing unit 308. Image processing unit 308 generates images and videos that are displayable on display 312. It is within the scope of the present description that display 312 include multiple displays or display systems (e.g. projection displays). An electrical signal (e.g. video signal) is transmitted from image processing unit 308 to display 312 by a second cable 314, which is any kind of electrical signal cable commonly known in the art. Image processing unit 308 can be in direct communication with multidimensional visualization module 316, which can also send electrical signals to display 312 via second cable 314. In one embodiment, image capture module 100, image processing unit 308, and multidimensional visualization module 316 are all housed in a single device or are physically one single device. Further, one or all of the components of the present invention can be manipulated by control panel 318 via cable network 320. In one embodiment, control panel 318 is wireless.

"Display," as used herein, can refer to any device capable of displaying a still or video image. Preferably, the displays of the present disclosure display HD still images and video images or videos which provide a surgeon with a greater level of detail than a SD signal. More preferably, the displays display such HD stills and images in stereoscopic 3D. Exemplary displays include HD monitors, cathode ray tubes, projection screens, liquid crystal displays, organic light emitting diode displays, plasma display panels, light emitting diodes, 3D equivalents thereof and the like. In some embodiments, 3D HD holographic display systems are considered to be within the scope of the present disclosure. In one embodiment, display 312 is a projection cart display system and incorporates the basic structural components of the Applicant's TrueVision Systems, Inc. stereoscopic image display cart described in the Applicant's co-pending U.S. application: Ser. No. 11/739,042. In another embodiment, display 312 is a high definition monitor, such as one or more liquid crystal displays (LCD) or plasma monitors, depicting a 3D HD picture or multiple 3D HD pictures.

The exemplary image processing units as illustrated in FIGS. 1, 2, and 3 include a microprocessor or computer configured to process data sent as electrical signals from image capture module 100 and to send the resulting processed information to display 312, which can include one or more visual displays for observation by a physician, surgeon or a surgical team. Image processing unit 308 may include control panel 318 having user operated controls that allow a surgeon to adjust the characteristics of the data from image capture module 100 such as the color, luminosity, contrast, brightness, or the like sent to the display.

In one embodiment, image capture module 100 includes a photosensor, such as a camera, capable of capturing a still image or video images, preferably in 3D and HD. However, the photosensor can also capture still images or video in 2D. It is within the teachings herein that the photosensor is capable of responding to any or all of the wavelengths of light that form the electromagnetic spectrum. Alternatively, the photosensor may be sensitive to a more restricted range of wavelengths including at least one wavelength of light outside of the wavelengths of visible light. "Visible light." as used herein, refers to light having wavelengths corresponding to the visible spectrum, which is that portion of the electromagnetic spectrum where the light has a wavelength ranging from about 380 nanometers (nm) to about 750 nm.

More specifically, the at least one data processor is also in direct communication with multidimensional visualization module 316 and/or image capture module 100. The data processors, in their basic form, are configured to produce at least one real-time virtual reference indicium including data for making at least one limbal and/or corneal relaxing incision in conjunction with the real-time visualization of at least a portion of the target surgical field produced by multidimensional visualization module 316. In one embodiment, the data processor or processors are incorporated into multidimensional visualization module 316. In another embodiment, at least one data processor is a stand alone processor such as a workstation, personal data assistant or the like.

The at least one data processor is controlled by built-in firmware upgradeable software and at least one user control input, which is in direct communication with the data processors. The at least one user control input can be in the form of a keyboard, mouse, joystick, touch screen device, remote control, voice activated device, voice command device, or the like and allows the surgeon to have direct control over the one or more virtual surgical reference indicium.

Figure 4:
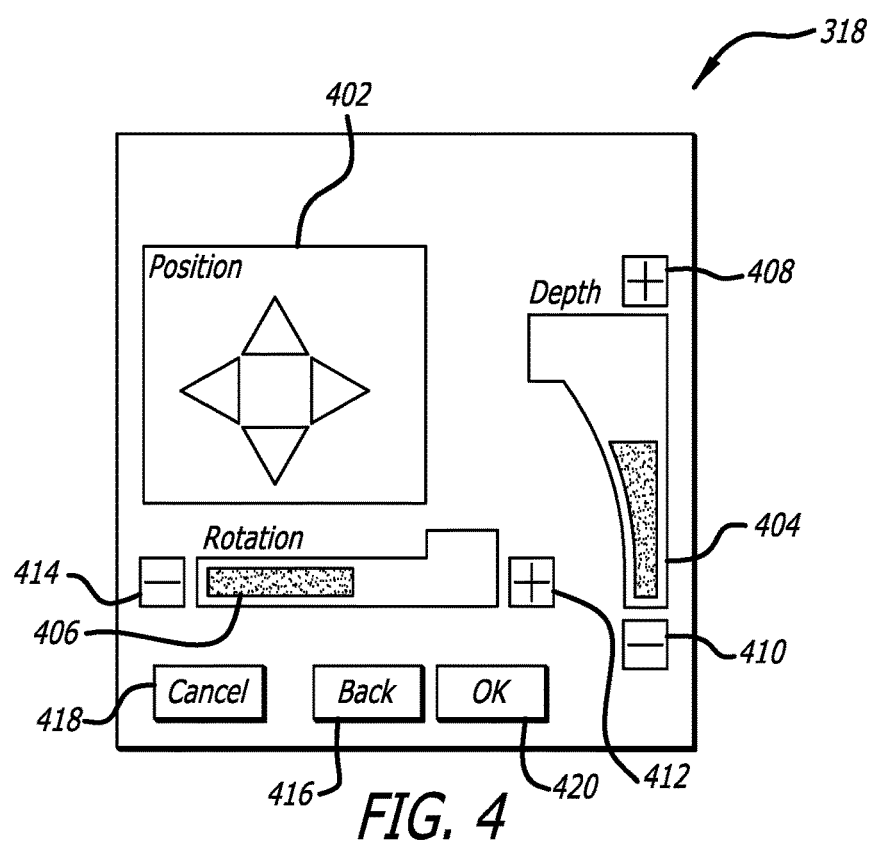
FIG. 4 is a plan view of an exemplary alignment control panel of the present description illustrating an exemplary embodiment of user input control thereof.

FIG. 4 illustrates an exemplary user control input, in the form of control panel 318. Control panel 318 includes multidirectional navigation pad 402 with user inputs allowing a controlling surgeon or operator to move data vertically, horizontally or any combination of the two. Additionally, the depth of the data can be adjusted using depth rocker 404 of control panel 318 and the rotation can be adjusted using rotation rocker 406 of control panel 318. Depth can be adjusted using both increase depth position 408 and decrease depth position 410 of depth rocker 404. Additionally, rotation can be adjusted using both increase rotation position 412 and decrease rotation position 414 of rotation rocker 406. Other non-limiting adjustments that can be made to the pre-operative image or to the real-time visualization include changes in diameter, opacity, color, horizontal and vertical size, and the like, as known in the art. It should be noted that in exemplary control panel 318 an adjustment can be undone by the surgeon utilizing "back" button 416. Further, the entire process can be ended by the surgeon by engaging "cancel" button 418. Further, once the surgeon is satisfied with the alignment of the data, the alignment is locked into place by engaging "ok" button 420.

Alternative control panel embodiments for the manipulation and alignment of the pre-operative still image are contemplated as being within the scope and teachings of the present description. For example, a hand-held device such as a 3D mouse can be used as known in the art to directly position templates, images, and references within the real-time multidimensional visualization. Such devices can be placed on a tabletop or held in mid-air while operating. In another embodiment, foot switches or levers are used for these and similar purposes. Such alternative control devices allow a surgeon to manipulate the pre-operative still image without taking his or her eyes off of the visualization of a surgical procedure, enhancing performance and safety.

In yet another alternative embodiment, a voice activated control system is used in place of, or in conjunction with, control panel 318. Voice activation allows a surgeon to control the modification and alignment of the pre-operative still image and its associated indicia as if he was talking to an assistant or a member of the surgical team. As those skilled in the art will appreciate, voice activated controls typically require a microphone and, optionally, a second data processor or software to interpret the oral voice commands. In yet a further alternative embodiment, a system is envisioned wherein the apparatus utilizes gesture commands to control pre-operative image adjustments. Typically, as known in the art, the use of gesture commands involves an apparatus (not shown) having a camera to monitor and track the gestures of the controlling physician and, optionally, a second data processor or software to interpret the commands.

In one embodiment, apparatus setup 300 can be used in many medical settings. For example, apparatus setup 300 can be used in an examination room. Therein, image capture module 102 utilizes photosensor 304 to capture pre-operative patient data such as still images, preferably in HD, and information relating to a patient's natural vertical axis. Photosensor 304 can be coupled to any piece of medical equipment that is used in an examination room setting wherein pre-operative data can be captured. Image capture module 100 directs this data to image processing unit 308. Image processing unit 308 processes the data received from image capture module 100 and presents it on display 312.

In another embodiment, apparatus setup 300 can be used in an operating room. Therein, image capture module 100 utilizes photosensor 304 to capture a real-time visualization of at least a portion of the target surgical field, preferably in HD, more preferably in 3D. However, a 2D real-time visualization of at least a portion of the target surgical field is also possible. Image capture module 100 directs this data to image processing unit 308 including multidimensional visualization module 316. Image processing unit 308 including multidimensional visualization module 316 processes the data received from image capture module 100 and presents it on display 312 in real-time.

In one exemplary embodiment, apparatus setup 300 is used in an operating room and photosensor 304 is a surgical microscope. Therein, image capture module 100 is retrofitted on the surgical microscope. The use of a surgical microscope in combination with apparatus setup 300 allows a surgeon to comfortably visualize a surgical procedure on one or more displays instead of staring for, in some cases, several hours though the eyepiece of a surgical microscope.

Apparatus setup 300 used in an examination room can be in direct communication with apparatus setup 300 used in the operating room. The two apparatus setups can be directly connected by cable, or indirectly connected through an intermediary device such as a computer server. In some embodiments, the two sections can be separate systems, even in different physical locations. Data can be transferred between the two systems by any means known to those skilled in the art such as an optical disc, a flash memory device, a solid state disk drive, a wired network connection, a wireless network connection or the like.

A further understanding of the present disclosure will be provided to those skilled in the art from an analysis of exemplary steps utilizing the apparatus described above to practice the associated methods disclosed herein.

Though the apparatus and associated methods are applicable to any type of surgery on any target structure or tissue, the exemplary features and advantages will be disclosed in the illustrative, but non-limiting context of ocular surgery, particularly astigmatism correction procedures using at least one limbal and/or corneal relaxing incision. This type of surgical procedure is quite common as astigmatism is present in about 65% of patients at levels of 0.5 diopter or more. Further, it is not uncommon for this type of procedure to accompany a cataract surgery wherein an intraocular lens (IOL) is implanted. For reference, there are over three million IOL implantation procedures done per year in the United States and astigmatism correction often accompanies this procedure.

The apparatus and methods described herein are useful as a standalone procedure to correct small to medium levels of astigmatism (generally below about 3 diopters, but can be used to correct up to 8 diopters). The apparatus and methods described herein are also specifically adaptable for use in addition to IOL implantation without modification. The apparatus and methods described herein can be used to guide a surgeon in making one or more limbal relaxing incisions and/or one or more corneal relaxing incisions.

Figure 5A:
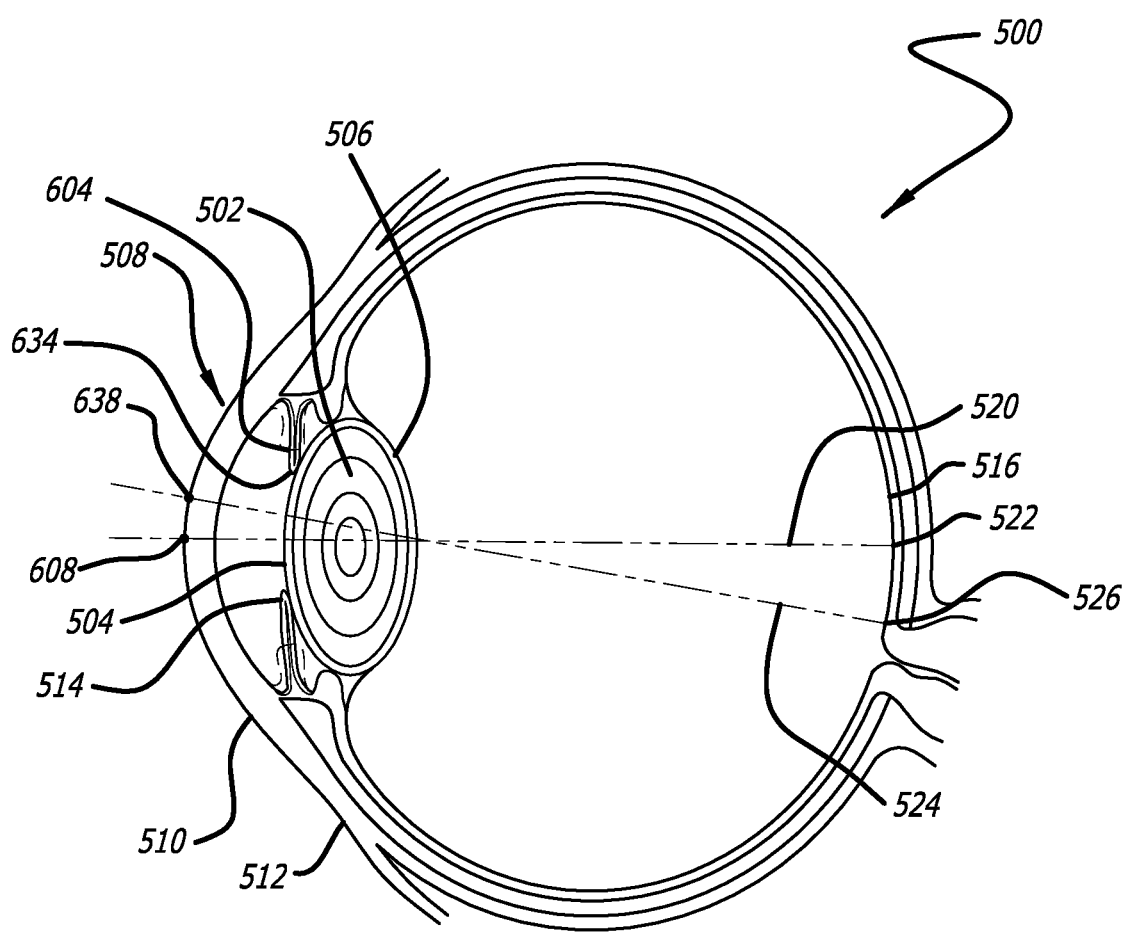
FIG. 5A is a cross-section of a human eye illustrating its structural elements and features.
Figure 5B:
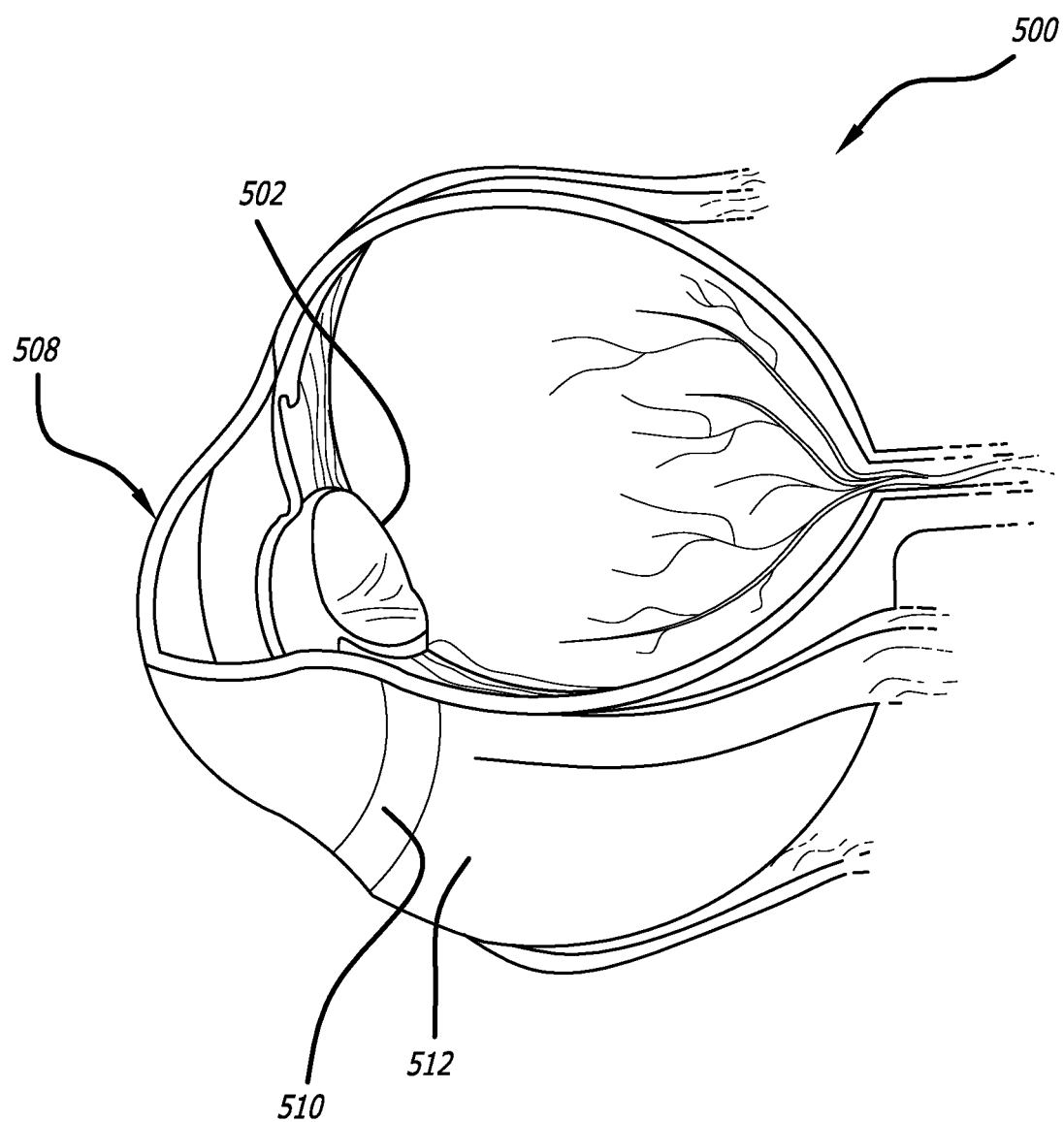
FIG. 5B is an angled perspective view of a human eye illustrating its structural elements and features.

Referring to FIG. 5A, a cross-sectional view of a general structure of eye 500 is provided. In FIG. 5B, an angled perspective view of eye 500 is provided Eye 500 contains natural crystalline lens 502 encased in anterior capsule 504 and posterior capsule 506. Eye 500 also includes cornea 508, the circumference of which is defined by limbus 510, which is the border between cornea 508 and the sclera 512. As light enters the eye through cornea 508, it passes through iris 514 and is focused by natural crystalline lens 502 at a focal point on retina 516.

Astigmatism occurs, in part, when cornea 508 and natural crystalline lens 502 do not properly focus light onto retina 516 at a focal point. Astigmatism is a vector with two components, vertical astigmatism and horizontal astigmatism. For example, a patient can have adequate focus in the horizontal plane, but have several diopters of astigmatism in the vertical plane. The opposite can also be true. However, in practice, it is generally a mix of astigmatism in the two planes that presents, and thus, astigmatism is defined along an axis or meridian between 0 and 180 degrees.

Differences in astigmatism generally result from imperfections in the curvature of cornea 508. In the last 20 years, advancements in ocular surgery have allowed the use of a rather non-invasive procedure to correct for small to moderate amounts of astigmatism. Initially, it was discovered that small incisions to cornea 508 could effectively result in reduction or in some cases complete elimination of astigmatism by effectively changing the curvature of cornea 508 thereby allowing light to properly be focused on retina 516. These incisions became known as corneal relaxing incisions. However, it was discovered that patients who underwent such procedures could develop side effects such as artifacts, haloes and problems with night vision. Despite the drawbacks of corneal relaxing incisions, they are still readily used by surgeons to correct for astigmatism.

As a result of the drawbacks and side effects of corneal relaxing incisions, procedures were developed wherein small incisions to limbus 510 at calculated positions could reduce or eliminate small to medium degrees of astigmatism without the side effects of corneal relaxing incisions. Cutting positions on the limbus allow the corneal tissue to relax and in effect changes the curvature of the cornea. These procedures have been named limbal relaxing incisions and have shown much promise in the field of ocular surgery as a result of their low degree of side effects and the relatively non-invasive nature of the procedures.

However, despite the success of limbal relaxing incision procedures, it is not uncommon for the procedure to be a trial and error procedure for a surgeon. Measured astigmatism data is commonly translated to incision cutting data using approximation formulas that have been developed over time and published for reference. Then, after incision cutting data has been generated, commonly in a pattern of one or more incision arcs to be cut, the surgeon either free hand cuts the incisions using best guess or stamps approximate arcs on the sclera to be incised using any appropriate marking tool known in the art.

Further, complicating matters and contributing to the possibility of less than optimal patient outcomes is a natural phenomenon of the human eye known as cyclorotation or cyclotorsion. Cyclorotation refers to the condition where, when a patient lays down from a generally vertical orientation into a supine or generally horizontal position, the patient's eyes rotate away from the measured vertical axis by a variable amount which ranges from about −12 to about +12 degrees. Because limbal relaxing incisions and corneal relaxing incisions need to be lined up with the vertical axis of an eye, it is important that the astigmatism data and resulting incision cutting data track the vertical axis of the eye.

With this understanding of the contemporary need for accurately and precisely placed, and rotationally accurate limbal relaxing incisions and corneal relaxing incisions, the following non-limiting, exemplary embodiments illustrate the previously unobtainable features and advantages of the apparatus and methods with relation to providing at least one accurate, real-time virtual reference indicium including data for making at least one limbal and/or corneal relaxing incision that can guide a surgeon in performing a properly and rotationally accurate relaxing incision or multiple incisions.

As a first step in an astigmatism correcting procedure according to the present description, a pre-operative data set is captured or obtained. The pre-operative data set can include any portion of data about a patient including, for example, the patient's weight, age, hair color, bodily features, medical history, and at least one image of at least a portion of the patient's target surgical anatomy, specifically the eye, information about axes of the eye of the patient, astigmatism data including steep k and flat k, and the like. According to one embodiment, the pre-operative data set includes the vertical axis of the patient's eye. The vertical axis as used herein is a measurement based at least partially on natural line of sight incorporating the patient's natural visual axis relative to changes in orientation of the target surgical field or the visual axis itself. A patient's natural vertical axis is indicated in chemically dilated eye 600 of FIG. 6A by vertical axis identifier 602.

In an exemplary embodiment, the pre-operative dataset, or pre-operative patient data includes a still image of at least a portion of the eye of the patient undergoing an astigmatism correcting procedure along with a measurement of the vertical axis of the patient's eye as well as data such as steep k and flat k. In some embodiments, the pre-operative still image is in HD. A pre-operative data set can also include a mark-up of the patient's eye for analysis, measurement, or alignment as well as topographical data or measurements.

It will be appreciated by those skilled in the art that the optical axis, and the visual axis of an eye are not necessarily synonymous or identical in fact they vary depending upon ambient light conditions and may diverge from one another depending on the nature of pupil dilation. "Dilation" of an eye is a retraction of the iris, opening the pupil of the eye and allowing more light to reach the retina. In most surgery conducted under bright lighting, pupil dilation is commonly accomplished using chemical dilating agents to relax the iris sphincter muscle thereby increasing the circumference of the iris to a maximal extent. In this manner the surgeon is provided with a clear view and subsequent access to internal structures of the eye.

Figure 6A:
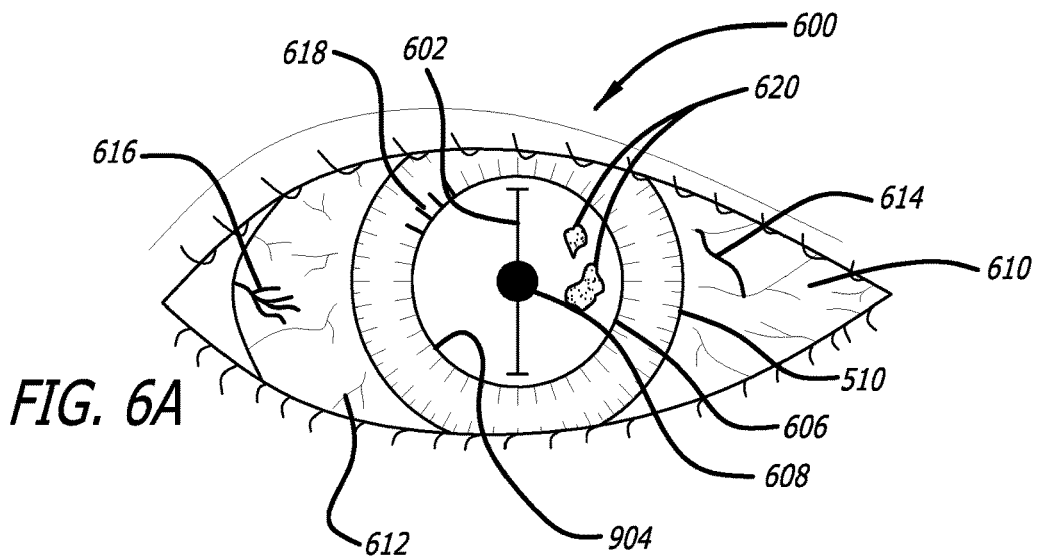
FIG. 6A is a front view of a human eye with a chemically dilated pupil illustrating the optical axis of the eye.

However, chemically induced pupil dilation produces a markedly different shaped pupil and pupillary boundary as well as a different pupillary center point location from that produced by natural dilation. For example, as illustrated in FIG. 6A (reference is also made to FIG. 5A), chemically dilated eye 600 has dilated iris 604 that produces a large, generally symmetrical pupil 606 concentric with the observed optical axis center point 608. This corneal center reference point is very close to that defined by the geometric center of the circle formed by the intersection of the patient's limbus 510. As depicted in FIG. 5A, optical axis 520 is defined by a line connecting the anterior pole, or optical axis center point 608, and the posterior poles, or retinal center point 522, of the eye. Further, the vertical axis of an eye is generally in an upright configuration as indicated by vertical axis identifier 602. As will be discussed, this vertical axis can shift, or reorient, depending on the patient's orientation.

Figure 6B:
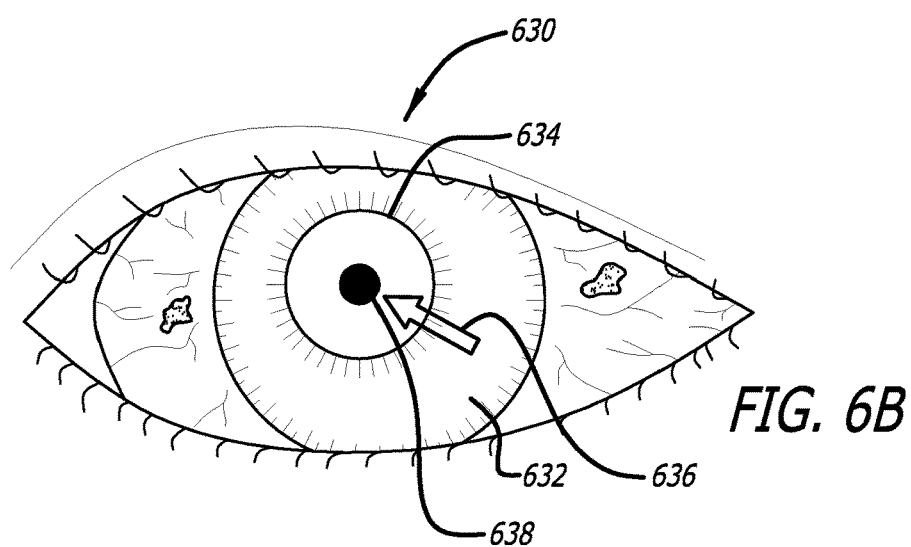
FIG. 6B is a front view of a human eye with a naturally dilated pupil illustrating the line of sight or the visual axis of the eye.

In contrast to symmetrical chemical dilation, naturally dilated eye 630, as shown in FIG. 6B, generally presents itself in low ambient light or no light conditions where natural dilated iris 632 naturally retracts to a lesser extent than under chemical dilation. More importantly, naturally dilated eye 630 is not symmetrical and produces asymmetrical pupil 634 that is generally biased nasally (towards the nose) and superiorly (up from center) as indicated by arrow 636 relative to symmetrical pupil 606 shown in FIG. 6A and is generally unique for each patient. As a result of this asymmetrical dilation, the patient's natural line of sight center point 638 as defined in the patient's cornea by the center of asymmetrical pupil 634 is also biased away from observed optical axis center point 608 observed under chemical dilation in FIG. 6A Therefore, under non-chemical dilation conditions, a patient's optical and visual axis corneal center points may not, and typically do not, line up.

This difference between an observed optical axis center point 608 and natural line of sight center point 638 is further illustrated by the cross-sectional view of eye 500 illustrated in FIG. 5A. There, the chemically-induced observed optical axis center point 608 is illustrated as being generally centrally disposed at the center of cornea 508 as defined by the chemically induced symmetrical pupil 606. In contrast, natural line of sight center point 638 is shown at a position that is generally nasally and superiorly biased away from observed optical axis center point 608 near the center of cornea 508 as defined by natural asymmetrical pupil 634. The resulting visual axis 524 passes through natural line of sight center point 638 and terminates at focal point 526 of eye 500. As those skilled in the art will appreciate, surgical procedures designed to improve or restore a patient's vision will be more effective if the procedures are based upon the patient's true or natural line of sight center point 638 as opposed to chemically induced observed optical axis center point 608 that has a lesser relation to how the patient's eye naturally focuses light to the high resolution focal point of the patient's retina at the fovea, or focal point 526. As will be discussed, the vertical axis identifier 602 can shift depending on the patient's orientation.

Figure 6C:
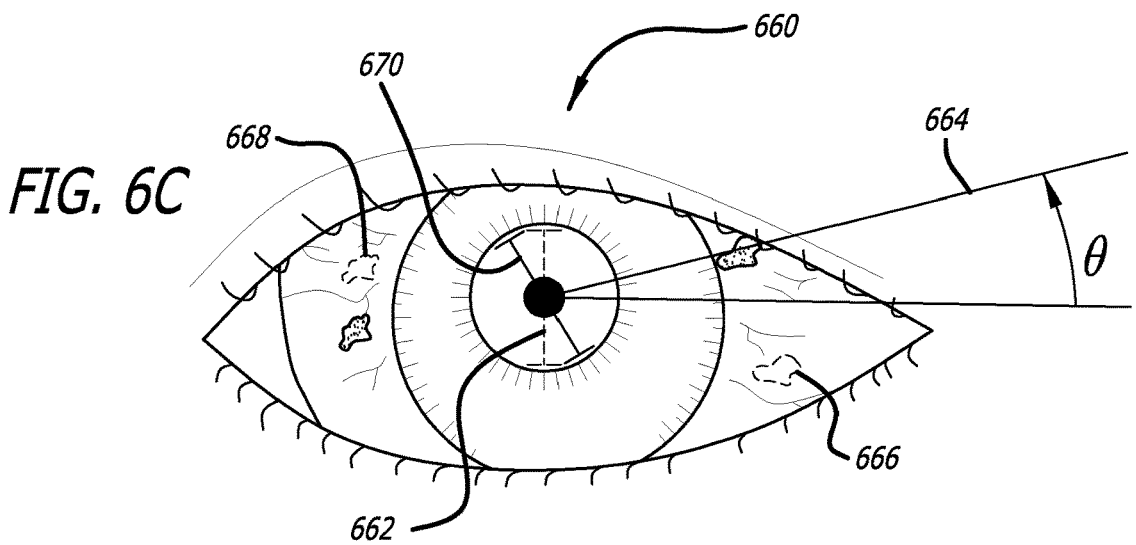
FIG. 6C is a front view of a human eye illustrating natural cyclorotation.

FIG. 6C illustrates this phenomenon of cyclorotation as eye 660 rotates away from the normal or originally measured vertical axis 662 by variable angle 664 when a patient assumes a prone or supine position. This rotation is further illustrated by the shifting of observable or visual scleral features 666 and 668 which also have rotated by variable angle 664. Thus, originally measured vertical axis 662 of the patient's eye, generally taken with the patient sitting in a vertical orientation, and any associated physical or structural aberrations and the resultant spherical distortions or astigmatism measured relative thereto, can differ from those of observed vertical axis 670, of the eye when the patient lays down into a supine or generally horizontal position, where most ocular surgeries take place, and the target eye cyclorotates into this displaced orientation. The present apparatus and methods make it possible for the surgeon to maintain the proper orientation, or rotational accuracy, of limbal relaxing incisions relative to the patient's originally measured vertical axis 662 by providing rotationally accurate reference indicia including data for making at least one limbal relaxing incision, which are aligned with observed vertical axis 670.

Prior to the presently disclosed apparatus and methods, it was the individual and variable skill of the surgeon at compensating for these natural physical differences between measured optical and vertical axis during the surgical procedure that determined the degree of post-operative success of the procedures involved in the ocular surgery and the resultant degree of patient satisfaction with the procedure.

The apparatus and methods of the present description provides a surgeon with the ability to create and use one or more user adjustable, accurate, real-time, virtual reference indicium including data for making at least one limbal and/or corneal relaxing incision which clearly and accurately take into account the natural vertical axis of the patient despite any shifting due to cyclorotation or asymmetrical dilation resulting from changes in the patient's physical positioning between pre-operative examination and surgery.

In one embodiment, wherein a pre-operative data set is collected, in order to properly measure the vertical axis of the eye, astigmatism data and other pre-operative data, a slit lamp microscope is used to collect the data. A "slit lamp" is an instrument commonly consisting of a high intensity light source that can be adapted to focus and shine the light as a slit A slit lamp allows an optometrist or ocular surgeon to view parts of the eye in greater detail than can be attained by the naked eye. Thus, a slit lamp can be used to view the cornea, retina, iris and sclera of a patient's eye or to identify the vertical, optical or visual axis of a patient's eye. A conventional slit lamp can be retro-fitted with an image capture module as described herein, preferably with at least one photosensor. This allows a surgeon or optometrist to comfortably collect accurate and reliable pre-operative patient data including at least one still image of the patient's eye, preferably under natural dilation and most preferably in HD.

In one embodiment, this is accomplished under natural dilation or with an un-dilated iris to clearly view and examine the patient's eye. This can also be accomplished in low ambient light because the exemplary visualization modules described herein are able to produce an accurate 3D HD image in at least one wavelength outside of the wavelengths of visible light. As an added benefit, collecting the pre-operative patient data under low ambient light conditions accurately identifies the vertical axis of the patient's eye for subsequent tracking and reference without sacrificing visual acuity for the physician.

In a second step, the pre-operative data set still image, or just still image, captured in the first step is matched to a real-time multidimensional visualization of at least a portion of the target surgical field. Matching the still image to the multidimensional visualization is important because the target surgical field may have changed since the pre-operative image still was captured such as by tissue shifting and rotating when the patient changes position. As a result, the measurements obtained during the pre-operative examination may no longer be accurate or easily aligned in light of such changes in the patient's physical alignment and position. Additionally, any surgical markings that may have been applied to the patient's tissues during the pre-operative examination may have shifted, been wiped away, or blurred.

At this point, the pre-operative still image of the patient's eye is analyzed by a surgeon, a surgical team or the at least one data processor of the apparatus to identify at least one distinct visible feature that is static and recognizable relative to and within the still image of the eye. Utilizing the teachings described herein, this at least one distinct visible feature is used to align the image with the real-time multidimensional visualization of the target surgical field during the actual surgery. Preferably, this real-time visualization is a 3D HD visualization of the target surgical field.

For example, referring to FIG. 6A, one or more exemplary distinct visible features that can be identified are illustrated in sclera 610 of eye 600. However, recognizable visible features can also be identified within the iris, on the cornea, or on the retina of the eye. Exemplary distinct visible features include, without limitation, surface vasculature 612, visible vascular networks 614 and vascular branching patterns 616, iris patterns 618, scratches on the cornea, dimples on the cornea, retinal features 620, deformities, voids, blotches, sequestered pigment cells, scars, darker regions, and combinations thereof. Additionally, both the pupillary boundary and limbus are distinct visible features, either of which can be utilized in accordance with the teachings of the present description to align and track the image in conjunction with the real-time visualization of the target surgical field.

In one embodiment, once at least one distinct visible feature has been identified in the pre-operative patient data still image, the still image and the associated visible feature or features are stored for later processing and use in the operating room. It should be noted that the pre-operative patient data need not be taken in a separate operation or at a separate location from the operating room or theater. For example, during surgery to repair a traumatic injury or to simplify a patients visit, the entire process can be performed in the operating room to save time.

A third step involves the surgeon, the surgical team, the at least one data processor, or a combination thereof aligning the pre-operative still image of the target surgical field with the real-time multidimensional visualization of the target surgical field. Generally speaking, this alignment is accomplished utilizing specific static visual features identified within the pre-operative still image of the target surgical site to align the still image with the real-time multidimensional visualization of the target surgical field. This allows the pre-operative image to be aligned accurately with the tissues of the target surgical field regardless of whether the target surgical field has shifted, rotated or reoriented relative to other patient tissues or structures following collection of the pre-operative data.

Figure 7:
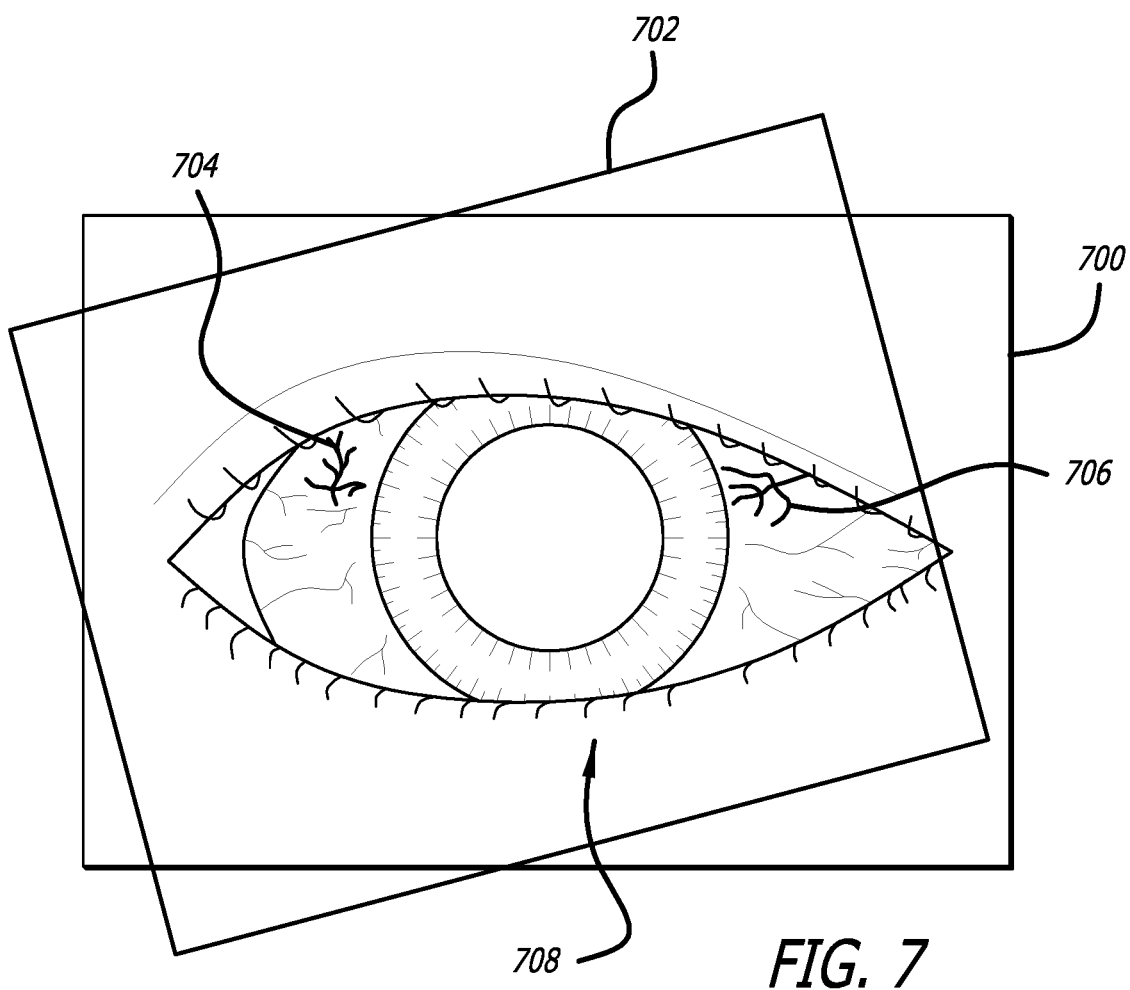
FIG. 7 is a front view of a human eye of a patient illustrating an exemplary embodiment of a real-time 3D HD visualization overlaid with an aligned HD pre-operative patient data still image of the patient eye.

The pre-operative still image of the patient's eye is overlaid on one or more real-time 3D HD visualizations of at least a portion of the patient's target surgical field for at least a portion of the surgical procedure. Referring to FIG. 7, exemplary real-time 3D HD visualization 700 of a patient's eye is overlaid with pre-operative patient data still image 702 of the same eye. Previously identified and recognizable distinct vascular networks in the sclera of the patient's eye, identified on the left as reference numeral 704 and on the right as reference numeral 706 of eye 708 are used to align pre-operative patient data still image 702 with real-time 3D HD visualization 700.

It should be noted that pre-operative patient data still image 702 is shown as being rotated relative to real-time 3D HD visualization 700, for example by a surgeon, to account for the naturally occurring cyclorotation of the patient's target eye as a result of the patient lying down for surgery. The previously identified distinct visual features 704 and 706 are used to rotate and align patient data still image 702 with the corresponding static visible structures of the patient's eye to maintain close alignment of the target site with the measured optical and visual axes and the associated structural and physical features of the patient's eye. Once the still image has been properly aligned either by a surgeon, a surgical team, at least one data processor or a combination thereof, the surgeon can lock the image in place.

In an optional fourth calibration step, the controlling surgeon places a calibration target having known dimensions and features into the real-time multidimensional visualization of the target surgical field and triggers the apparatus to calibrate the target surgical field into consistent and useful measurable dimensions.

In a further step, the at least one data processor incorporates at least one real-time, virtual reference indicium or multiple reference indicia including data for making at least one limbal relaxing incision, corneal relaxing incision, or a combination thereof into the real-time visualization of the target surgical field. The virtual reference indicia including data for making at least one limbal and/or corneal relaxing incision can be highly patient specific. For example, in some embodiments, the indicia including data for making at least one limbal and/or corneal relaxing incision can include pre-determined shapes, such as, but not limited to, arcs, lines, circles, ellipses, squares, rectangles, trapezoids, diamonds, triangles, polygons, and irregular volumes including specific information pertaining to the incisions to be made to correct the eye's astigmatism.

Although in the present exemplary embodiment, the virtual surgical reference indicia including data for making at least one limbal and/or corneal relaxing incision are incorporated into a real-time visualization after alignment of the still image, in other embodiments, the virtual surgical reference indicia including data for making at least one limbal and/or corneal relaxing incision are added as early as the capturing of the pre-operative still image. It is within the scope of the present description that the virtual surgical reference indicia including data for making at least one limbal and/or corneal relaxing incision may be incorporated at any point up until the indicia are needed during a surgical procedure. For example, the virtual surgical reference indicia including data for making at least one limbal and/or corneal relaxing incision can be added directly on the pre-operative still image instantly after it is captured.

It is also within the scope of the present disclosure that a surgeon may input one or more freehand virtual surgical reference indicia on a still image or real-time multidimensional visualization Additionally, it is also contemplated as being within the scope of the present description to utilize pre-operative markings that are placed within the target surgical field on the patient so that the data processor will generate virtual surgical reference indicia including data for making at least one limbal and/or corneal relaxing incision according to the markings found on the pre-operative data set.

Further still, a surgeon may utilize multiple different virtual surgical reference indicia including data for making at least one limbal and/or corneal relaxing incision during a single surgical procedure or any subpart thereof. For example, initial reference indicia including data for making at least one limbal and/or corneal relaxing incision may be replaced by other reference indicia including data for making at least one limbal and/or corneal relaxing incision at any point during a surgery, or two or more different indicia may be used to represent more complex surgical markings.

Even further still, the at least one virtual reference indicia including data for making at least one limbal and/or corneal relaxing incision can be tailored to a surgeons particular needs. Incision shapes, lengths and thicknesses are based on both inputted astigmatism data and algorithms used by the surgeon to generate them. The astigmatism correction algorithm used by the surgeon can be tailored or can be replaced by any appropriate re-calculated algorithm known in the art.

It should also be noted that when desired to correspond to a real-time 3D HD visualization of the target surgical field, the real-time virtual surgical reference indicia including data for making at least one limbal and/or corneal relaxing incision can be generated in 3D as well as in HD, or both, depending on the particular surgical procedure or upon the needs of the surgeon. In some embodiments, either the real-time virtual reference indicia or data for making at least one limbal and/or corneal relaxing incision can be in 3D and/or HD and vice versa. For example, and not intended to be a limitation, a 3D HD real-time virtual reference indicia can be paired with 2D standard definition data for making at least one limbal and/or corneal relaxing incision.

As described above in reference to FIG. 7, once pre-operative patient data still image 702 has been locked in place over real-time 3D HD visualization 700 of the target surgical field, the apparatus incorporates at least one real-time, virtual surgical reference indicia including data for making at least one limbal and/or corneal relaxing incision into the combined aligned pre-operative patient data still image 702 with real-time 3D HD visualization 700 of the patient's eye to function as a precise and rotationally accurate surgeon controlled reference indicia to facilitate the surgeon's making of at least one appropriately sized, shaped and positioned limbal or corneal relaxing incision that will assist in producing superior post-surgical results and patient satisfaction.

It should be noted that it is within the scope and teachings of the present disclosure that the virtual surgical reference indicia including data for making at least one limbal and/or corneal relaxing incision can be sized and modified according to the needs of the surgeon. For example, the indicium including data for making at least one limbal relaxing incision can be sized, rotated and moved horizontally, vertically, and in depth as needed by the surgeon.

Further, the virtual surgical reference indicia including data for making at least one limbal and/or corneal relaxing incision can be composed of different types of indication markings and can be in HD. For example, without limitation, the markings can be monochromatic or colored, with varying levels of transparency, composed of thin or thick lines, dashed or solid lines, a series of different shapes and the like as is consistent with contemporary digital graphics technology. Further, the graphic presentation can be different within individual indicia to more easily visualize the indicium in different areas or to emphasize specific areas of interest.

Figure 8:
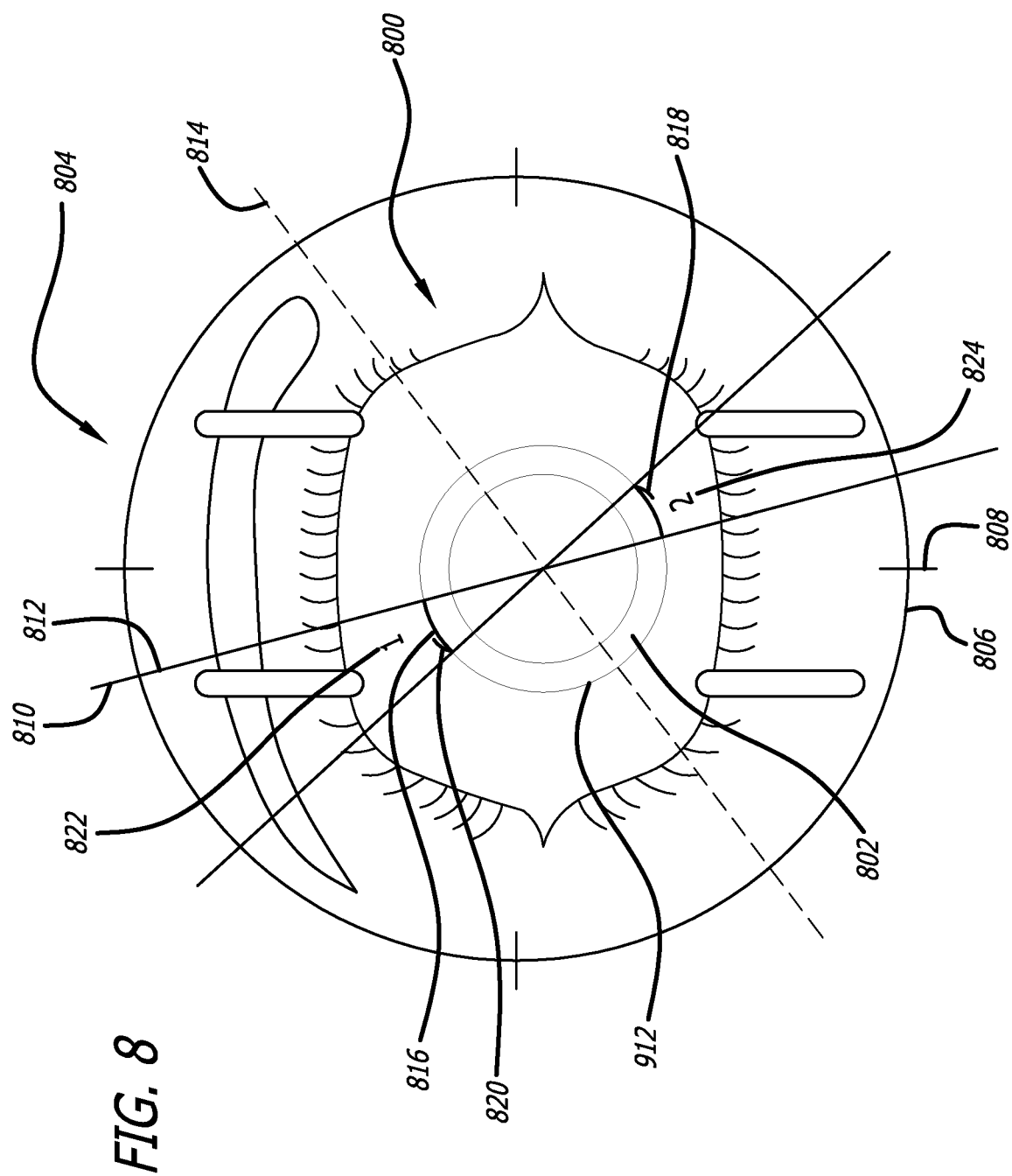
FIG. 8 is a chemically dilated eye with a generated indicium including data for making two limbal relaxing incisions and other alignment features.

Since the virtual reference indicia including data for making at least one limbal and/or corneal relaxing incision described herein can track the vertical axis of a patient's eye, such indicia can be particularly useful for astigmatism correction procedures. Referring to FIG. 8, eye 800 is chemically dilated as evidenced by symmetrically dilated iris 802. In one embodiment, indicium including data for making at least one limbal relaxing incision 804 has a substantially circular shape. It should be noted that indicium including data for making at least one limbal relaxing incision 804 can have any shape that may be useful for an astigmatism correcting procedure. Other shapes that can be useful include, but are not limited to ellipses, squares, rectangles, diamonds, stars, trapezoids and the like. Combinations of shapes may also be useful. Indicium including data for making at least one limbal relaxing incision 804 includes compass card 806. In one embodiment, compass card 806 can include one or more graduated markings 808 for orientation reference. Graduated markings 808, can include information such as, but not limited to, degree markings, limit information, minimum and maximum settings, true patient axis markings and the like.

Further, indicium including data for making at least one limbal relaxing incision 804 includes accurate information about the patient's natural vertical axis. For example, cross-hatch 810 can be used to track the natural vertical axis of a patient's eye. Cross-hatch 810 includes vertical member 812 and can optionally include horizontal member 814. It is most common for vertical member 812 to track the natural vertical axis of a patient's eye. The identification means for tracking the vertical axis of the eye does not have to be of the form of cross-hatch 810, but can be as simple as a straight solid line, a dashed line or the like.

Indicium including data for making at least one limbal relaxing incision 804 further includes one or more guides for making limbal relaxing incisions. In one embodiment illustrated in FIG. 8, two guides can be used. Therein, first guide 816 and second guide 818 aid the surgeon in making rotationally accurate incisions in order to correct for astigmatism in the patient. First guide 816 and second guide 818 can optionally include one or more arrow indicator 820 which further assists the surgeon in making an incision in an optimal direction. Indicium including data for making at least one limbal relaxing incision 804 can further include first numeral 822 and second numeral 824 which can be used by a surgeon to make two or more incisions in a particular order and can be any sequential numbering system, for example, whole numbers, Roman numerals, letters and the like. Even further still, first guide 816 and second guide 818 can include a first and second guide line to indicate the beginning and end of an incision. If the cuts are to be symmetric, the lines are made of two lines intersecting at the center of the chemically dilated pupil. This ensures that the cuts will be symmetric.

Figure 9:
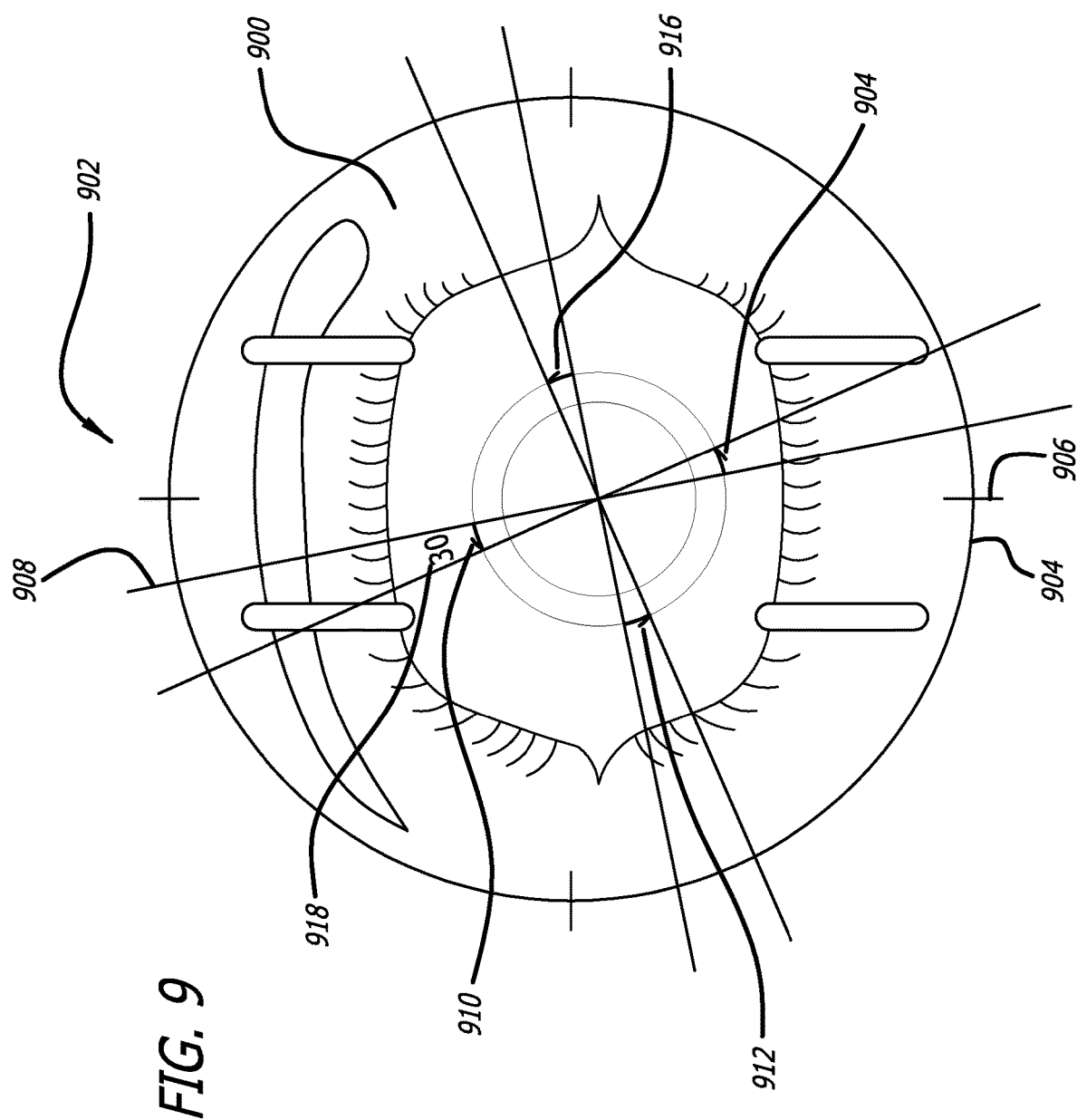
FIG. 9 is a chemically dilated eye with another alternate indicium including data for making four limbal relaxing incisions and other alignment features.

In another exemplary embodiment, illustrated in FIG. 9 is an eye 900 requiring four limbal relaxing incisions to correct astigmatism. Again, second indicium including data for making at least one limbal relaxing incision 902 includes compass card 904, graduated markings 906, and cross-hatch 908 for tracking the vertical axis. Second indicium including data for making at least one limbal relaxing incision 902 includes first guide 910, second guide 912, third guide 914 and fourth guide 916 all of which can include optional arrows and numerals for guiding a surgeon in the correct order of incision and direction of cut. Additionally illustrated in FIG. 9 is degree designation 918 wherein the total degree distance of a cut is indicated. These features can be inserted into any indicium described herein at the discretion of the surgeon Again, in FIG. 9, all four guides are flanked by cross-hatch lines to indicate the beginning and end of the cut and the lines intersect at the center of the pupil to ensure symmetry of the limbal relaxing incisions.

Figure 10:
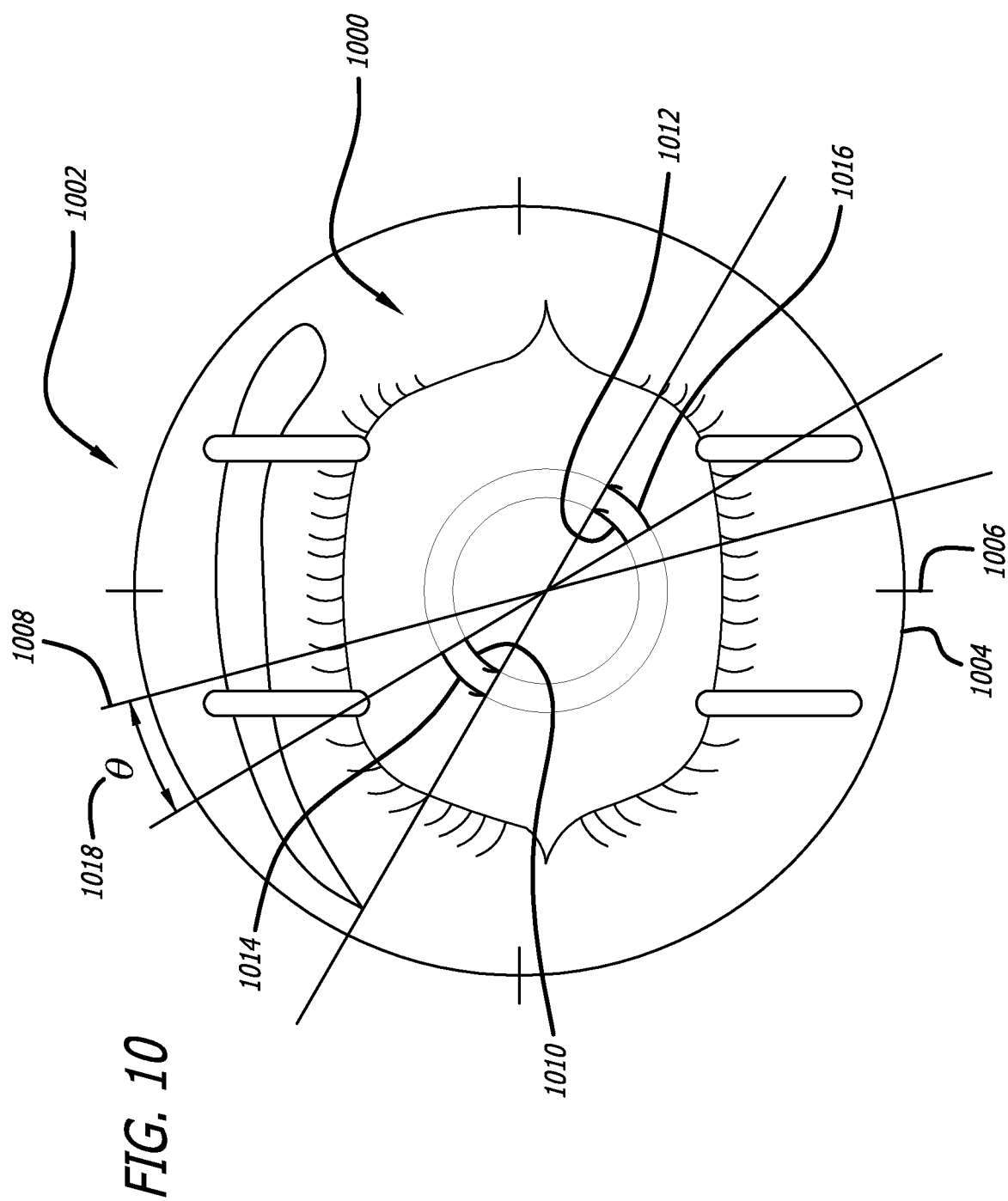
FIG. 10 is a chemically dilated eye with another indicium including data for making two sets of limbal relaxing incisions and other alignment features.

In still another exemplary embodiment, illustrated in FIG. 10 is eye 1000 requiring four limbal relaxing incisions to correct astigmatism. Again, third indicium including data for making at least one limbal relaxing incision 1002 includes compass card 1004, graduated markings 1006, and cross-hatch 1008 for tracking the vertical axis Third indicium including data for making at least one limbal relaxing incision 1002 includes first guide 1010, second guide 1012, third guide 1014 and fourth guide 1016 all of which can include optional arrows and numerals for guiding a surgeon in the correct order of incision and direction of cut in third indicium including data for making at least one limbal relaxing incision 1002, first guide 1010 and third guide 1014 are back to back as are second guide 1012 and fourth guide 1016. Additionally third indicium including data for making at least one limbal relaxing incision 1002 includes guides that do not begin at the vertical axis, but rather are displaced by variable angle 1018. These features can be inserted into any indicium described herein at the discretion of the surgeon Again, in FIG. 10, all four guides are flanked by cross-hatch lines to indicate the beginning and end of the cut and the lines intersect at the center of the pupil to ensure symmetry of the limbal relaxing incisions.

Figure 11:
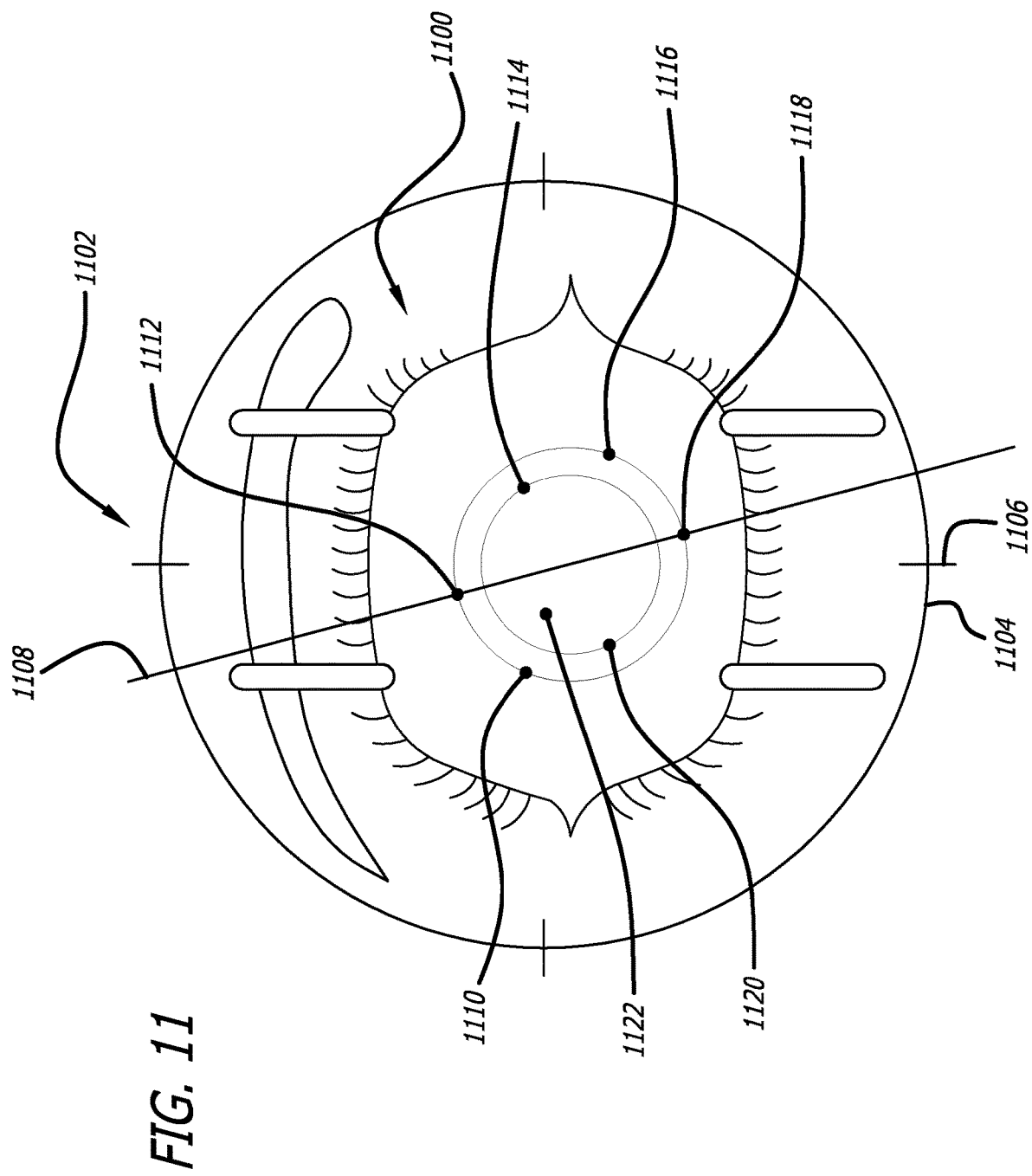
FIG. 11 is a chemically dilated eye with an indicium including data for making limbal relaxing incisions and a corneal relaxing incision in the form of spots and other alignment features.

FIG. 11 illustrates an embodiment wherein a laser is used to incise spots into regions of the limbus or even in the cornea to correct astigmatism. Eye 1100 requires six limbal relaxing incisions and one corneal relaxing incision in the form of laser spots to correct astigmatism. Again, forth indicium including data for making at least one limbal and corneal relaxing incision 1102 includes compass card 1104, graduated markings 1106, and cross-hatch 1108 for tracking the vertical axis. Forth indicium including data for making at least one limbal and corneal relaxing incision 1102 includes first limbal guide spot 1110, second limbal guide spot 1112, third limbal guide spot 1114, fourth limbal guide spot 1116, fifth limbal guide spot 1118, sixth limbal guide spot 1120 and seventh corneal guide spot 1122 all of which can include numerals for guiding a surgeon in the correct order of incision. Guide spots do not need to be symmetrical and can be placed into a template before the indicium is aligned and then subsequently aligned with the vertical axis of the eye.

Figure 12:
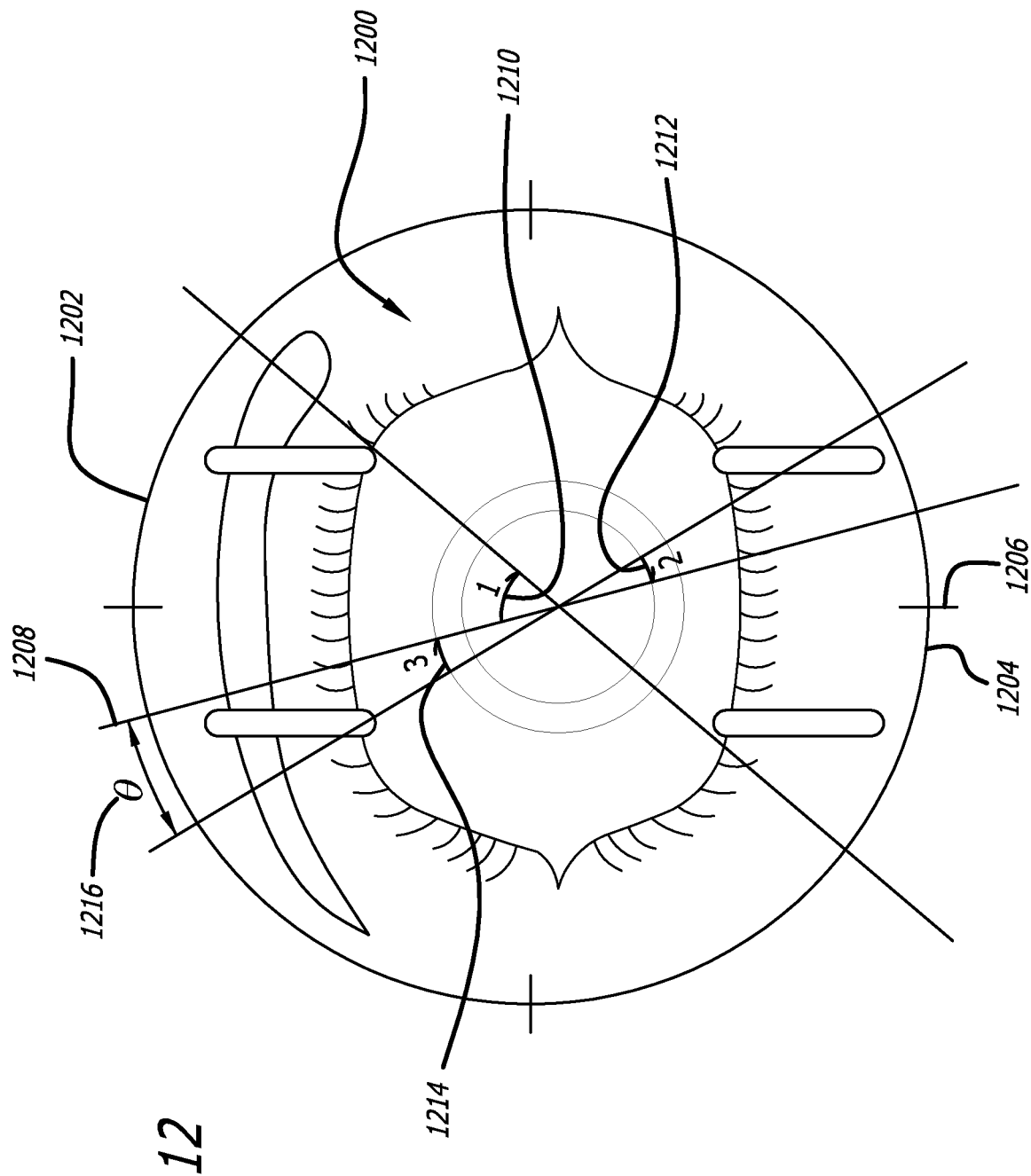
FIG. 12 is a chemically dilated eye with another indicium including data for making limbal and corneal relaxing incisions.

In yet another exemplary embodiment, illustrated in FIG. 12 is eye 1200 requiring two limbal relaxing incisions and one corneal relaxing incision to correct for astigmatism. Again, fifth indicium including data for making at least one limbal and/or corneal relaxing incision 1202 includes compass card 1204, graduated markings 1206, and cross-hatch 1208 for tracking the vertical axis. Third indicium including data for making at least one limbal and/or corneal relaxing incision 1202 includes first corneal guide 1210, second limbal guide 1212 and third limbal guide 1214 all of which can include optional arrows and numerals for guiding a surgeon in the correct order of incision and direction of cut. In fifth indicium including data for making at least one limbal and/or corneal relaxing incision 1202, first corneal guide 1210, second limbal guide 1212 and third limbal guide 1214 are randomly located based on a surgeons recommendation. Additionally fifth indicium including data for making at least one limbal and/or corneal relaxing incision 1202 includes guides that do not begin or end at the vertical axis, but rather are displaced by variable angle 1216. These features can be inserted into any indicium described herein at the discretion of the surgeon.

Typically, once at least one rotationally accurate indicium including data for making at least one limbal and/or corneal relaxing incision has been added to a real-time visualization of the target surgical field and is properly aligned with the vertical axis, a surgeon can make the proper limbal and/or corneal relaxing incisions to correct for astigmatism.

A surgeon will find that the apparatus and methods disclosed herein provide many advantages over existing technology. Firstly, as ocular surgeons are aware, incision markings commonly associated with limbal and/or corneal relaxing incisions to correct astigmatism are hard to estimate with the naked eye, and even if markings are made on the eye itself, those markings are not commonly effective once a procedure has commenced. The present disclosure provides apparatus and methods which assist a surgeon in aligning with rotational accuracy at least one limbal and/or corneal relaxing incision with the vertical axis of an eye by providing easy to see real-time virtual indicia including data for making at least one limbal and/or corneal relaxing incision.

Further, the reference indicium or indicia including data for making at least one limbal and/or corneal relaxing incision are not affected by the surgical procedure itself. Therefore, they remain as constant references even when the target tissues are subjected to fluids and wiping. More importantly, the indicia including data for making at least one limbal and/or corneal relaxing incision are precise, rotationally accurate and tissue and structure specific, rather than the approximations known in the art. Further, the indicium can be changed, removed, and reinstated as needed to provide an added degree of control and flexibility to the performance of a surgical procedure. For example, a controlling surgeon can chose to vary the transparency or remove a reference indicium including data for making at least one limbal relaxing incision altogether from a visualization to give a more clear view of underlying tissues or structural features and then reinstate the indicium to function as a template or guide for astigmatism correction.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed No language in the specification should be construed as indicating any non-claimed element essential to the practice of the invention.

Groupings of alternative elements or embodiments of the invention disclosed herein are not to be construed as limitations Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications. Each of the above-cited references is individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for guiding an astigmatism correction procedure on an eye of a patient, the method comprising:
   receiving, from a first photosensor, a pre-operative still image of an ocular target surgical site of the patient prior to the astigmatism correction procedure;
   producing a virtual indicium that includes data for guiding the astigmatism correction procedure in conjunction with the pre-operative still image such that the virtual indicium is rotationally accurate with respect to the ocular target surgical site displayed within the pre-operative still image;
   receiving from a real-time, multidimensional visualization module a real-time multidimensional visualization of the ocular target surgical site during the astigmatism correction procedure;
   aligning the pre-operative still image including the rotationally accurate virtual indicium with the multidimensional visualization; and
   displaying the multidimensional visualization of the ocular target surgical site in conjunction with the rotationally accurate virtual indicium.

2. The method according to claim 1, further comprising:
obtaining the pre-operative still image of the patient prior to cyclorotation of the eye when the patient lies down for surgery.

3. The method according to claim 1, wherein aligning the pre-operative still image with the multidimensional visualization includes:
determining a specific visual feature within the ocular target surgical site within the pre-operative still image;
identifying the specific visual feature within the multidimensional visualization; and
rotating, moving, and positioning the pre-operative still image such that the specific visual feature of the pre-operative still image is overlaid on top of the specific visual feature of the ocular target surgical site included within the multidimensional visualization.

4. The method according to claim 3, further comprising:
including in the specific visible feature at least one of a vasculature, a vascular network, a vascular branching pattern, a pattern in an iris, a scratch on a cornea, a dimple on the cornea, a retinal feature, a limbus, a pupillary boundary, a deformity, a void, a blotch, a sequestered pigment cell, a scar, an intentionally placed marking, and a dark region.

5. The method according to claim 1, further comprising:
incorporating information in the virtual indicium for making at least one limbal relaxing incision, at least one corneal relaxing incision, at least one astigmatic keratotomy incision, or a combination thereof, and wherein the astigmatism correction procedure includes at least one of a limbal relaxing incision, a corneal relaxing incision, an astigmatic keratotomy incision and an intra-ocular lens implantation incision.

6. The method according to claim 1, further comprising:
causing at least one of the multidimensional visualization, the pre-operative still image, and the virtual indicium to be stereoscopic.

7. The method according to claim 1, further comprising:
displaying the virtual indicium in conjunction with the multidimensional visualization after detecting that the pre-operative still image is locked into place with the multidimensional visualization.

* * * * *